(12) United States Patent
Nishida et al.

(10) Patent No.: US 12,013,365 B2
(45) Date of Patent: Jun. 18, 2024

(54) VIRUS MEASURING METHOD, VIRUS MEASURING DEVICE, VIRUS DETERMINING PROGRAM, STRESS DETERMINING METHOD, AND STRESS DETERMINING DEVICE

(71) Applicant: OSAKA UNIVERSITY, Osaka (JP)

(72) Inventors: Kohji Nishida, Osaka (JP); Noriyasu Hashida, Osaka (JP); Masateru Taniguchi, Osaka (JP); Makusu Tsutsui, Osaka (JP)

(73) Assignee: OSAKA UNIVERSITY, Osaka (JP)

(*) Notice: Subject to any disclaimer, the term of this patent is extended or adjusted under 35 U.S.C. 154(b) by 759 days.

(21) Appl. No.: 17/258,662

(22) PCT Filed: Jul. 18, 2019

(86) PCT No.: PCT/JP2019/028356
§ 371 (c)(1),
(2) Date: Jan. 7, 2021

(87) PCT Pub. No.: WO2020/017608
PCT Pub. Date: Jan. 23, 2020

(65) Prior Publication Data
US 2021/0285911 A1    Sep. 16, 2021

(30) Foreign Application Priority Data
Jul. 19, 2018 (JP) .................................. 2018-135961

(51) Int. Cl.
*G01N 27/327* (2006.01)
*G01N 27/447* (2006.01)
(Continued)

(52) U.S. Cl.
CPC ....... *G01N 27/3278* (2013.01); *G01N 27/447* (2013.01); *G01N 33/48721* (2013.01); *G01N 33/56983* (2013.01)

(58) Field of Classification Search
CPC ................................................ G01N 33/48721
See application file for complete search history.

(56) References Cited

U.S. PATENT DOCUMENTS 8,494,782 B1 * 7/2013 Stolc .................... C12Q 1/6869
702/19
2008/0280283 A1 11/2008 Kondo
(Continued)

FOREIGN PATENT DOCUMENTS

EP        1544310 A2 *  6/2005  ............... C12Q 1/68
JP     2000-275248 A    10/2000
(Continued)

OTHER PUBLICATIONS

EPO machine-generated English language translation WO 2017183716 A1, patented Oct. 26, 2017 (Year: 2017).*
(Continued)

*Primary Examiner* — Alexander S Noguerola
(74) *Attorney, Agent, or Firm* — Dilworth & Barrese, LLP

(57) ABSTRACT

Provided are a virus measuring method, a virus measuring device, a virus determining program, a stress determining method, and a stress determining device. A virus measuring method includes a contact step of bringing a liquid specimen containing a body fluid of a subject and an electrolytic solution into contact with each other via a through-hole portion formed in a separating wall, a current measuring step of applying a voltage to the liquid specimen and the electrolytic solution with respect to the through-hole portion and obtaining a waveform of an ionic current flowing through the through-hole portion, and a virus determining step of (Continued)

determining the kind of a virus contained in the body fluid on the basis of the waveform. In the virus determining step, the kind of the virus is determined by comparing the waveform with waveform information that corresponds to a known virus and is obtained beforehand.

10 Claims, 12 Drawing Sheets

(51) Int. Cl.
*G01N 33/487* (2006.01)
*G01N 33/569* (2006.01)

(56) References Cited

U.S. PATENT DOCUMENTS

| | | | |
|---|---|---|---|
| 2010/0292101 A1* | 11/2010 | So | C12Q 1/6869 506/23 |
| 2014/0374255 A1 | 12/2014 | Hongo et al. | |
| 2017/0074855 A1* | 3/2017 | Morin | G01N 33/54366 |
| 2018/0155768 A1 | 6/2018 | Cohen | |
| 2018/0185345 A1 | 7/2018 | Faller | |
| 2018/0202969 A1* | 7/2018 | Zhang | C12N 9/16 |
| 2018/0275088 A1 | 9/2018 | Huff et al. | |
| 2019/0012888 A1 | 1/2019 | Gordon | |
| 2019/0119747 A1 | 4/2019 | Nishida et al. | |
| 2019/0257787 A1 | 8/2019 | Washio et al. | |
| 2020/0225210 A1 | 7/2020 | Zhao et al. | |
| 2020/0270686 A1 | 8/2020 | Nishida et al. | |

FOREIGN PATENT DOCUMENTS

| | | | | |
|---|---|---|---|---|
| JP | 2007-331263 A | 12/2007 | | |
| JP | 2009-072313 A | 4/2009 | | |
| JP | 2012-047735 A | 3/2012 | | |
| JP | 2017-156168 A | 9/2017 | | |
| JP | 2018-517757 A | 7/2018 | | |
| WO | 2006/006634 A1 | 1/2006 | | |
| WO | WO 2013116509 A1 * | 8/2013 | | C12Q 1/68 |
| WO | 2013/137209 A1 | 9/2013 | | |
| WO | WO 2014027968 A1 * | 2/2014 | | G01N 27/40 |
| WO | 2017/170571 A1 | 10/2017 | | |
| WO | 2017/170572 A1 | 10/2017 | | |
| WO | 2017/183716 A1 | 10/2017 | | |
| WO | WO 2017183716 A1 * | 10/2017 | | G01N 15/12 |
| WO | 2018/067878 A1 | 4/2018 | | |
| WO | 2018/081178 A1 | 5/2018 | | |
| WO | 2018/110540 A1 | 6/2018 | | |

OTHER PUBLICATIONS

CDC—Key Facts about Influenza (Flu), author unknown, Oct. 24, 2022 (Year: 2022).*

PubChem—3-Sialyllactose, author unknown downloaded Oct. 14, from https://pubchem.ncbi.nlm.nih.gov/compound/3_-Sialyllactose (Year: 2023).*

English language translation of Written Opinion for international application No. PCT/JP2019/028356 dated Oct. 15, 2019 (Year: 2019).*

English language translation of Tsutsu et al., "Identifying single influenza virus using solid-state nanopores", Lecture preprints of teh 78th JSAP Autum Meeting 2017. (Year: 2017).*

Extended European Search Report from European Patent Applicaiton No. 19837472.0 dated Jul. 26, 2021.

Kessler et al., "Short screening scales to monitor population prevalences and trends in non-specific psychological distress"; Psychological Medicine, 2002, 32: 959-976.

Tsutsui et al., "Identifying single influenza virus using solid-state nanopores"; Lecture preprints of the 78th JSAP Autumn Meeting, 2017.

Taniguchi et al., "Convergence of machine learning and single molecule analysis"; Lecture preprints of the 65th JSAP Spring Meeting, 2018.

Tsutsui et al., "Identification of Individual Bacterial Cells through the Intermolecular Interactions with Peptide-Functionalized Solid-State Pores," Analytical Chemistry 2018, 90: 1511-1515.

Tsutsui et al., "Discriminating single-bacterial shape using low-aspect-ratio pores", Scientific Reports, 2017, 7: 17371-1 to 17371-9.

Tsutsui et al., "Particle Trajectory-Dependent Ionic Current Blockade in Low-Aspect-Ratio Pores", ACS NANO, 2016 10: 803-809.

Arima et al., "Identification of virus by means of nanopore measurement", Lecture preprints of the 79th JSAP Autumn Meeting, 2018.

* cited by examiner

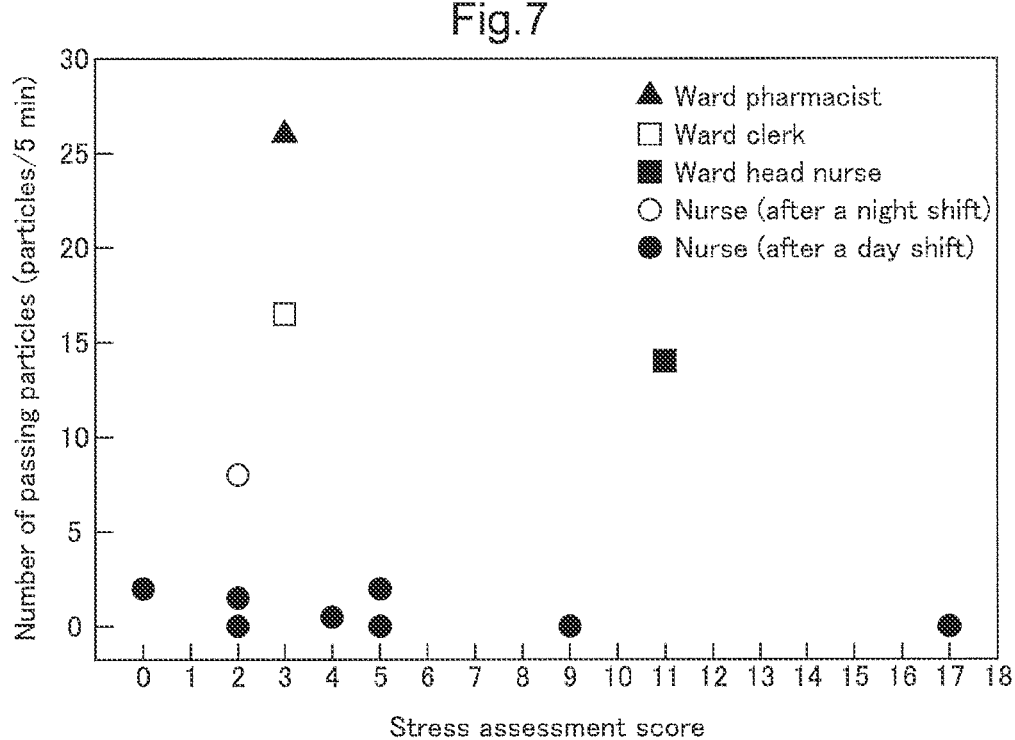

Fig.8

* During the past month or so (during the past 30 days), how often did you have the following feelings?

Date of Completion:
Heisei Year   /Month   /Day of Week

1) How often did you feel nervous (anxious about something trivial)?
   0: None of the time; 1: A little of the time; 2: Some of the time; 3: Most of the time; 4: All of the time 2) How often did you feel hopeless?
   0: None of the time; 1: A little of the time; 2: Some of the time; 3: Most of the time; 4: All of the time 3) How often did you feel restless or fidgety?
   0: None of the time; 1: A little of the time; 2: Some of the time; 3: Most of the time; 4: All of the time 4) How often did you feel so depressed that nothing could cheer you up?
   0: None of the time; 1: A little of the time; 2: Some of the time; 3: Most of the time; 4: All of the time 5) How often did you feel that everything was an effort (bother)?
   0: None of the time; 1: A little of the time; 2: Some of the time; 3: Most of the time; 4: All of the time 6) How often did you feel worthless?
   0: None of the time; 1: A little of the time; 2: Some of the time; 3: Most of the time; 4: All of the time

VIRUS MEASURING METHOD, VIRUS MEASURING DEVICE, VIRUS DETERMINING PROGRAM, STRESS DETERMINING METHOD, AND STRESS DETERMINING DEVICE

TECHNICAL FIELD

The present invention relates to a virus measuring method, a virus measuring device, a virus determining program, a stress determining method, and a stress determining device.

BACKGROUND ART

Patent Document 1 discloses a method of judging whether or not there is a possibility of a subject having chronic stress, the method including measuring the saliva cortisol concentration and making the judgement using the measured concentration. The cortisol concentration is measured using, for example, liquid chromatography.

Patent Document 2 discloses a method of assessing the level of fatigue that accompanies everyday life or a disease by measuring the amount of human herpesvirus in a body fluid of a subject. According to this assessment method, if the amount of human herpesvirus in the body fluid is high, the subject is assessed to be in a state of chronic fatigue. Human herpesvirus 6, human herpesvirus 7, human cytomegalovirus, and Epstein-Barr virus are listed as examples of the human herpesvirus. Blood, saliva, cerebrospinal fluid, and urine are listed as examples of the body fluid. A method in which the amount of viral DNA is measured using PCR is described as an example of the method for measuring the amount of virus. As disclosed in Patent Documents 1 and 2, stress and fatigue level (hereinafter, these will be collectively referred to simply as "stress") of a subject can be assessed by measuring a component of a body fluid of the subject.

Patent Document 3 discloses a single particle analyzing device and a single particle analysis method. A measuring vessel of this single particle analyzing device includes a first chamber and a second chamber defined by an insulating membrane, and the membrane has a pore opening that connects the first chamber and the second chamber to each other. A first electrode that is connected to the ground and exposed in the first chamber and a second electrode that is connected to the ground and exposed in the second chamber are provided in the measuring vessel. An ammeter and a power source are provided between the electrode that is exposed in the second chamber and the ground. This single particle analyzing device measures a signal that is detected between the first and the second electrodes when a particle contained in a liquid filled in the first chamber passes through the pore opening, thereby measuring the shape of the particle.

Patent Document 4 discloses a biomarker for stress diseases that is detected from a specimen obtained from a biological fluid such as urine, blood, saliva, or cerebrospinal fluid sampled from a mammal with a stress disease. Irritable bowel syndrome is given as an example of the stress disease.

Patent Document 5 discloses a method and a composition for treating herpesvirus-induced diseases. Patent Document 5 states that herpesviruses can induce autoimmune or inflammatory diseases.

Non-Patent Document 1 discloses a mood or anxiety disorder survey sheet for assessing stress by means of a questionnaire (interview). The mood or anxiety disorder survey sheet is known as a so-called K6 survey sheet. The K6 survey sheet has been proposed for the purpose of screening for mental illness (so-called mental health conditions) such as depression and anxiety disorders, and is widely used, in surveys of general populations, as an indicator of the severity of certain mental issues including psychological stress. With regard to cutoff scores for determining the presence or absence or the severity of mental issues, the following four score ranges are set: Negative: 0-4; Mild: 5-8; Intermediate: 9-12; and Severe: 12-24.

CITATION LIST

Patent Literature

Patent Document 1: JP 2000-275248A
Patent Document 2: WO 2006/006634
Patent Document 3: WO 2013/137209
Patent Document 4: JP 2012-047735A
Patent Document 5: JP 2018-517757T

Non-Patent Literature

Non-Patent Document 1: Kessler R C, Andrews G, COLPE L J, et al. Short screening scales to monitor population prevalances and trends in non-specific psychological distress, Psychological Medicine 2002; 32(6): 959-76

SUMMERY OF INVENTION

Technical Problem

The stress determination methods disclosed in Patent Documents 1 and 2 use, for example, cortisol or herpesvirus as a so-called stress marker. In order to measure such a stress marker, it is necessary to use a time- and labor-consuming measurement method such as liquid chromatography or PCR. Also, these measurement methods have the problem of detection limit. For example, even PCR, which is said to be highly sensitive, is not capable of detecting a virus unless 40 or more virus particles are present per microliter, and is therefore inconvenient. Moreover, virus detection is not feasible until the conditions become severe (a state in which the virus has multiplied), and there is a problem in that early diagnosis and treatment of a disease (a state of being under intense stress, or a stress disease) cannot be sufficiently performed.

The method for assessing stress by means of a questionnaire disclosed in Non-Patent Document 1 depends on self-report by subjects and their sensibility, and the results are therefore variable. For this reason, there are cases where correct diagnosis of a disease cannot be made. For example, there is a problem in that the assessment result does not reflect a stress state that a subject is not aware of. It is thus demanded that a simple, rapid, and accurate method for determining stress should be provided.

Furthermore, as disclosed in Patent Document 4, stress is directly related to diseases. It is commonly known that excessive stress can trigger diseases. Also, it is commonly known that a disease itself can cause stress on the body and mind. Moreover, as disclosed in Patent Document 5, herpesviruses can induce various diseases. It is thus demanded that a method for identifying or identifying a state of pathological stress and a stress disease, as well as various diseases correlated or related thereto, by determining the kind of virus or measuring (counting) the number of virus particles.

The present invention was made in view of the above-described circumstances, and it is an object thereof to provide a virus measuring method with which stress, a stress state, and a stress disease, as well as various diseases that are correlated or related thereto can be determined or identified in a simple and rapid manner; a virus measuring device that implements the virus measuring method; a virus determining program; a stress determining method; and a stress determining device that implements the stress determining method.

Solution to Problem

A characteristic feature of a virus measuring method according to the present invention for achieving the above-described object lies in that the method includes:
- a contact step of bringing a liquid specimen containing a body fluid of a subject and an electrolytic solution into contact with each other via a through-hole portion formed in a separating wall;
- a current measuring step of applying a voltage to the liquid specimen and the electrolytic solution with respect to the through-hole portion and obtaining a waveform of an ionic current flowing through the through-hole portion; and
- a virus determining step of determining the kind of a virus contained in the body fluid on the basis of the waveform,
- wherein, in the virus determining step, the waveform is compared with waveform information that corresponds to a known virus and is obtained beforehand, and the kind of the virus is determined within 10 minutes.

With the above-described configuration, if the body fluid contains a virus, when a voltage is applied to the liquid specimen and the electrolytic solution, the waveform of the ionic current flowing through the through-hole portion changes. With the above-described configuration, on the basis of the change in the waveform of the ionic current and the waveform information corresponding to a known virus, the kind of the virus contained in the body fluid of the subject (patient) is determined within 10 minutes.

With the above-described configuration, the kind of virus can be determined on the basis of the waveform of the ionic current corresponding to at least one virus particle, and therefore, the kind of virus can be determined with high speed, high sensitivity, and high accuracy, compared with PCR.

The concept of the kind of virus to be determined includes the viral species, that is, the "family", such as the difference between herpesvirus and influenza virus, and the "type", such as the difference between herpes simplex virus 1 and human herpesvirus 6, as well as the difference in the "activity (state)" between viruses of the same kind or the same type. The concept of activity includes the so-called viability of the virus, for example, a state in which the virus is infectious (referred to as "viable", "infectious virus", or the like) and a state in which the virus is inactivated/is no longer infectious (referred to as "non-viable", "inviable", "non-infectious", or the like).

As a result of the kind of virus being determined, a doctor can obtain information for use in identification of a disease in the subject. Also, as a result of the kind of virus being determined, the doctor can obtain information for use in understanding the state of the disease in the subject by, for example, counting the number of virus particles for each kind of virus.

Furthermore, since the kind of virus is determined within 10 minutes, rapid disease identification by the doctor can be facilitated. As a result of rapid disease identification being achieved, the doctor can prevent the disease in the subject from becoming severe, and can reduce the burden (e.g., waiting time) on the subject. In addition, the effect of the treatment administered by the doctor can be increased, and the subject can recover early.

With the above-described configuration, the waveform information corresponding to a known virus is obtained beforehand. Therefore, with the above-described configuration, the kind of the virus contained in the body fluid of the subject can be determined by comparing the newly obtained waveform with the waveform information that has been obtained beforehand. For example, when the newly obtained waveform is compared with and matches the waveform information on a known virus that has been obtained beforehand, it is determined that the same kind of virus as the known virus is present. When the newly obtained waveform is compared with and does not match the waveform information on a known virus that has been obtained beforehand, it is determined that the virus contained in the body fluid is not of the same kind as the known virus. Note that waveform information corresponding to a plurality of known viruses may be obtained beforehand as the waveform information corresponding to a known virus.

Another characteristic feature of the virus measuring method according to the present invention lies in that the current measuring step includes a passing step of causing a microparticle contained in the body fluid to electrophoretically migrate and pass through the through-hole portion.

With the above-described configuration, microparticles contained in the body fluid, or in other words, microparticles contained in the liquid specimen electrophoretically migrate and pass through the through-hole portion. When a microparticle passes through the through-hole portion, a change corresponding to each virus particle occurs in the waveform of the ionic current. On the basis of the waveform (change in the waveform) of the ionic current at the time when the microparticle passes through the through-hole portion and the waveform information corresponding to a known virus, the kind of the virus contained in the body fluid of the subject is determined within 10 minutes.

With the above-described configuration, the kind of the virus contained in the body fluid of the subject can be determined by comparing the waveform that is obtained when a microparticle passes through the through-hole portion with the waveform information that is obtained beforehand. For example, when the newly obtained waveform is compared with and matches the waveform information on a known virus that has been obtained beforehand, it is determined that the microparticle corresponding to the newly obtained waveform is a virus particle of the same kind of virus as the known virus. When the newly obtained waveform is compared with and does not match the waveform information on a known virus that has been obtained beforehand, it is determined that the microparticle corresponding to the newly obtained waveform is not a virus particle of the same kind of virus as the known virus.

Another characteristic feature of the virus measuring method according to the present invention lies in that the known virus is a herpesvirus.

The above-described configuration makes it possible to determine whether or not the microparticle corresponding to the newly obtained waveform is a herpesvirus particle.

Another characteristic feature of the virus measuring method according to the present invention lies in that the body fluid is selected from tear fluid and intraocular fluid.

With the above-described configuration, the kind of a virus leaking into tear fluid or intraocular fluid can be identified, and the identified kind of virus can be provided as information for use in diagnosis of a disease caused by the virus. This information is particularly useful as information for diagnosis of especially an eye disease, a stress state, or a stress disease. Note that tear fluid is a body fluid that can be easily and noninvasively collected. For this reason, in the case where tear fluid is collected as the body fluid, the burden on the subject during specimen collection can be reduced. Note that "intraocular fluid" is the fluid that fills the eyeball. The concept of intraocular fluid includes the fluid that fills at least the chamber of the eye, and the vitreous body (vitreous humor).

Another characteristic feature of the virus measuring method according to the present invention lies in that the current measuring step includes a separation step of separating a virus contained in the body fluid and impurities other than the virus contained in the body fluid using an electroosmotic flow.

For example, when causing microparticles contained in the body fluid to migrate due to electrophoresis, if, for example, the migrating distance is increased (a long flow channel is formed as a migration path), it is possible to separate virus particles having a particularly high negative surface charge from microparticles having a low negative surface charge. With such a configuration in which a virus contained in the body fluid is separated from impurities other than the virus contained in the body fluid using an electroosmotic flow, virus particles having a particularly high negative surface charge among microparticles contained in the body fluid selectively pass through the through-hole portion. On the other hand, the other microparticles having a low negative surface charge are inhibited from passing through the through-hole portion by the electroosmotic flow that occurs in the through-hole portion and flows in the opposite direction to the migrating direction of the microparticles.

Another characteristic feature of the virus measuring method according to the present invention lies in that a disease is identified on the basis of the kind of the virus that has been determined in the virus determining step.

With the above-described configuration, one or more diseases estimated from the kind of virus that has been determined are identified. As a result of the disease(s) being identified, the diagnosis and treatment of the disease(s) by the doctor can be facilitated.

A characteristic feature of a virus measuring device according to the present invention for achieving the above-described object lies in that the device includes: a specimen reservoir that stores a liquid specimen containing a body fluid of a subject; an electrolytic solution reservoir that stores an electrolytic solution; a separating wall portion that separates the specimen reservoir and the electrolytic solution reservoir; a through-hole portion that is formed in the separating wall portion and through which the specimen reservoir and the electrolytic solution reservoir are in communication with each other; a measuring unit that applies a voltage to the liquid specimen and the electrolytic solution and obtains a waveform of an ionic current flowing through the through-hole portion; a storage unit in which a learned model is stored, the learned model being created by performing machine learning so that, when the waveform is input to the learned model, the learned model outputs a viral species corresponding to waveform information on a known viral species; and a virus determining unit that applies the waveform obtained from the measuring unit to the learned model read from the storage unit and thereby determines the kind of a virus contained in the body fluid.

With the above-described configuration, the above-described virus measuring method can be implemented. More specifically, when a voltage is applied to the liquid specimen stored in the specimen reservoir and the electrolytic solution stored in the electrolytic solution reservoir, an ionic current flows via the through-hole portion of the separating wall portion. The measuring unit measures this ionic current and can thereby obtain the waveform of the ionic current corresponding to a microparticle (virus) contained in the body fluid of the subject. When the waveform is obtained, the virus determining unit further applies the waveform obtained by the measuring unit to the learned model, and accurately determines the kind of the virus contained in the body fluid. Note that this learned model is an example of the waveform information corresponding to a virus. The application of the waveform to the learned model is an example of comparison of the waveform with the waveform information.

As a result of the kind of virus being determined, the doctor can obtain information for use in identification of a disease in the subject. Also, as a result of the kind of virus being determined, the doctor can obtain information for use in understanding the state of the disease in the subject by, for example, counting the number of virus particles for each kind of virus.

With the above-described configuration, the probability of a correct viral species being output can be increased by reinforcing the learned model beforehand. Thus, the speed of determination by the virus determining unit can be easily increased. For example, the determination speed can be increased to such an extent that the kind of virus can be determined within 10 minutes. This can facilitate rapid disease identification by the doctor. As a result of rapid disease identification being achieved, the disease can be prevented from becoming severe, the effect of the treatment administered by the doctor can be increased, and the subject can recover early.

A characteristic feature of a virus measuring device according to the present invention for achieving the above-described object lies in that the device includes: a specimen reservoir that stores a liquid specimen containing a body fluid of a subject, the body fluid being selected from tear fluid and intraocular fluid; an electrolytic solution reservoir that stores an electrolytic solution; a separating wall portion that separates the specimen reservoir and the electrolytic solution reservoir; a through-hole portion that is formed in the separating wall portion and through which the specimen reservoir and the electrolytic solution reservoir are in communication with each other, the through-hole portion having hydrophilicity; a measuring unit that applies a voltage to the liquid specimen and the electrolytic solution and obtains a waveform of an ionic current flowing through the through-hole portion; a storage unit in which waveform information on a known viral species is stored; and a virus determining unit that determines the kind of a virus contained in the body fluid on the basis of the waveform, wherein the virus determining unit determines the kind of the virus contained in the body fluid by comparing the waveform obtained from the measuring unit with the waveform information on the known viral species read from the storage unit.

With the above-described configuration, the above-described virus measuring method can be implemented when a liquid specimen containing a body fluid of the subject selected from tear fluid and intraocular fluid is used. More specifically, since the through-hole portion has hydrophilicity, the through-hole portion can be quickly filled with the liquid specimen and become capable of conducting an ionic current. Then, when a voltage is applied to the liquid specimen stored in the specimen reservoir and the electrolytic solution stored in the electrolytic solution reservoir, an ionic current flows via the through-hole portion of the separating wall portion. The measuring unit measures this ionic current and can thereby obtain the waveform of the ionic current corresponding to a microparticle (virus) contained in the body fluid of the subject. The kind of the virus contained in the body fluid of the subject can be accurately determined by the virus determining unit comparing this waveform with the waveform information on a known virus stored in the storage unit.

With the above-described configuration, the waveform of the ionic current changes each time a virus particle passes through the through-hole portion (for each virus particle), and therefore, the kind of virus can be determined with high speed and high sensitivity, compared with PCR.

For example, when the virus determining unit compares the newly obtained waveform with the waveform information on a known virus that has been obtained beforehand, and the waveform matches the waveform information, it is determined that the microparticle corresponding to the newly obtained waveform is a virus particle of the same kind of virus as the known virus. When the virus determining unit compares the newly obtained waveform with the waveform on a known virus that has been obtained beforehand, and the waveform does not match the waveform information, it is determined that the microparticle corresponding to the newly obtained waveform is not a virus particle of the same kind of virus (viral species) as the known virus. Note that waveform information corresponding to a plurality of known viruses may be stored in the storage unit as the waveform information corresponding to a known virus.

Another characteristic feature of the virus measuring device according to the present invention lies in that the liquid specimen contains oxiglutathione.

With the above-described configuration, the activity of the virus contained in the body fluid of the subject is improved, or a decrease in the activity of the virus is prevented. As a result, the accuracy of determination of the kind of a virus contained in the body fluid of the subject improves.

Another characteristic feature of the virus measuring device according to the present invention lies in that the virus determining unit determines the kind of the virus within 10 minutes, and the virus measuring device is portable.

With the above-described configuration, the virus measuring device is portable. Thus, the doctor can freely carry the virus measuring device to wherever it is needed, whenever it is needed. Therefore, when there is a patient who is a subject, the diagnosis and treatment of a disease that the doctor performs by determining the kind of virus at a location where the test imposes less burden on the patient can be facilitated.

With the above-described configuration, since the kind of virus is determined within 10 minutes, rapid disease identification by doctor can be facilitated. As a result of rapid disease identification being achieved, the disease can be prevented from becoming severe, the effect of the treatment administered by the doctor can be increased, and the subject can recover early.

A characteristic feature of a virus determining program for causing a computer to execute processing for determining the kind of a virus contained in a body fluid of a subject according to the present invention for achieving the above-described object lies in that the processing includes: receiving a waveform of an ionic current obtained by applying a voltage to a liquid specimen containing the body fluid and an electrolytic solution; determining the kind of the virus contained in the body fluid on the basis of the waveform that has been received by the receiving processing; and transmitting a determination result that has been obtained by the virus determining processing, wherein, in the virus determining processing, the kind of the virus is determined on the basis of a learned model, the learned model being created by performing machine learning so that, when the waveform is input to the learned model, the learned model outputs a viral species corresponding to waveform information on a known viral species.

With the above-described configuration, it is possible to cause a virus measuring device serving as the computer (hereinafter, referred to simply as the "CPU") to execute processing for determining the kind of the virus contained in the body fluid of the subject. More specifically, with the above-described configuration, it is possible to cause the CPU to execute the receiving processing of receiving the waveform of the ionic current, the virus determining processing of determining the kind of the virus contained in the body fluid on the basis of the received waveform, and the transmitting processing of transmitting the determination result.

With the above-described configuration, when causing the CPU to execute the virus determining processing, the CPU is caused to execute processing of applying the received waveform to the learned model and determining the kind of the virus contained in the body fluid. Thus, determination of the kind of virus based on the learning result of machine learning can be implemented.

A characteristic feature of a stress determining method according to the present invention for achieving the above-described object lies in that the method includes: a contact step of bringing a liquid specimen containing a body fluid of a subject and an electrolytic solution into contact with each other via a through-hole portion formed in a separating wall; a current measuring step of applying a voltage to the liquid specimen and the electrolytic solution with respect to the through-hole portion and obtaining a waveform of an ionic current flowing through the through-hole portion; and a stress determining step of determining a stress state of the subject by comparing the waveform with predetermined stress state information.

Various substances can leak into the body fluid of the subject depending on the state of stress of the subject. In the following description, a substance that leaks depending on the state of stress of the subject will be referred to as a "stress marker". Note that the term "body fluid" refers to a liquid, such as tear fluid or saliva, that naturally exudes, or is excreted, from the human body to the outside. With the above-described configuration, the state of leakage of the stress marker can be obtained as a waveform of an ionic current (hereinafter, also referred to simply as the "waveform"). More specifically, a predetermined stress marker is caused to migrate from the liquid specimen toward the electrolytic solution by applying a predetermined voltage to the liquid specimen and the electrolytic solution. When the stress marker passes through the through-hole portion, the ionic current flowing between the liquid specimen and the electrolytic solution changes. Thus, a waveform corresponding to the state of leakage of the stress marker can be obtained. The thus obtained waveform corresponds to the level of stress of the subject. The waveform can be obtained in an extremely simple and rapid manner, compared with analytical methods such as PCR or liquid chromatography.

The stress state information is information in which a waveform of a predetermined ionic current is associated with a state of stress (e.g., a state in which stress has built up) of a person. Note that the "state of stress" is an indicator such as a stress score that is objectively understood from, for example, the working environment of a person, such as the occupation or job, duties, working hours, and time of day worked. Therefore, with the above-described configuration, the stress state of the subject can be determined by comparing the waveform with the predetermined stress state information. Unlike self-report, this determination is not affected by sensibility, and is therefore accurate.

Another characteristic feature of the stress determining method according to the present invention lies in that the current measuring step includes a passing step of causing a microparticle contained in the body fluid to electrophoretically migrate and pass through the through-hole portion, the determining step includes a counting step of counting the number of microparticles that have passed through the through-hole portion on the basis of the waveform, and a comparing step of comparing the counted number of microparticles with the stress state information, and the stress state information contains relation information on a relation between the number of microparticles contained in the body fluid and stress intensity.

With the above-described configuration, microparticles (e.g., herpesvirus particles) contained in the body fluid can be cause to migrate and pass through the through-hole portion by electrophoresis. When a microparticle passes through the through-hole portion, a change occurs in the waveform. Thus, on the basis of such a change in the waveform, the number of microparticles contained in the body fluid of the subject can be counted.

In addition, with the above-described configuration, when relation information (e.g., a calibration curve) on the relation between the stress intensity and the number of microparticles contained in a human body fluid is obtained beforehand as the stress state information, the intensity of stress of the subject can be determined on the basis of the number of microparticles contained in the body fluid of the subject.

Another characteristic feature of the stress determining method according to the present invention lies in that the microparticle is a herpesvirus particle.

Many adults are infected with a herpesvirus. If stress of a person increases, the state of the immune system changes with the increase in stress, and as a result, a herpesvirus leaks into a body fluid. Thus, with the above-described configuration, the stress state of the subject can be determined in a simple and rapid manner by directly measuring the number of herpesvirus particles in the body fluid of the subject. In addition, unlike self-report, the determination is not affected by sensibility, and is therefore accurate.

Another characteristic feature of the stress determining method according to the present invention lies in that the body fluid is tear fluid.

Tear fluid is a body fluid that can be easily and noninvasively collected. For this reason, the burden on the subject can be reduced. For example, tears can be directly collected using a pipette or the like, or it is also possible to flush the eye and collect a flushing solution containing tears.

In addition, microparticles in the tear fluid correspond well to the stress state of the subject, and therefore, detection sensitivity improves. For example, a herpesvirus establishes latent infection in ganglia, such as the trigeminal ganglion, of the body. The trigeminal nerve is one of the cranial nerves, and the ophthalmic nerve that controls the human eye is included in the trigeminal nerve. For this reason, the latent herpesvirus in the trigeminal ganglion is likely to leak into tear fluid that exudes from the lacrimal gland of the eye. Moreover, if the intensity of stress of the subject increases, the herpesvirus leaks into tear fluid even more. Thus, with the above-described configuration, simple and rapid stress determination can be achieved by using tear fluid as the body fluid.

A characteristic feature of a stress determining device according to the present invention for achieving the above-described object lies in that the device includes: a specimen reservoir that stores a liquid specimen containing a body fluid of a subject; an electrolytic solution reservoir that stores an electrolytic solution; a separating wall portion that separates the specimen reservoir and the electrolytic solution reservoir; a through-hole portion that is formed in the separating wall portion and through which the specimen reservoir and the electrolytic solution reservoir are in communication with each other; a measuring unit that applies a voltage to the liquid specimen and the electrolytic solution and obtains a waveform of an ionic current flowing through the through-hole portion: a storage unit in which stress state information corresponding to the waveform is stored; and a stress determining unit that determines a stress state of the subject, wherein the stress determining unit determines a stress state of the subject by comparing the waveform obtained from the measuring unit with the stress state information read from the storage unit.

With the above-described configuration, the above-described stress determining method can be implemented. More specifically, when a voltage is applied to the liquid specimen stored in the specimen reservoir and the electrolytic solution stored in the electrolytic solution reservoir, an ionic current flows via the through-hole portion of the separating wall portion. The measuring unit measures this ionic current and can thereby obtain a state of leakage of the stress marker as a waveform of the ionic current. The stress state of the subject can be determined by comparing this waveform with the stress state information.

Another characteristic feature of the stress determining device according to the present invention lies in that the stress determining unit has a counting unit that counts the number of microparticles contained in the body fluid that have passed through the through-hole portion due to electrophoresis on the basis of the waveform, and a comparing unit that compares the counted number of microparticles with the stress state information, and the stress state information contains relation information on a relation between the number of microparticles contained in the body fluid and stress intensity.

When a voltage is applied to the liquid specimen stored in the specimen reservoir and the electrolytic solution stored in the electrolytic solution reservoir, microparticles contained in the body fluid migrate due to electrophoresis. When a microparticle migrating due to electrophoresis passes through the through-hole portion, a change occurs in the waveform of the ionic current. Based on such a change in the waveform of the ionic current, the counting unit counts the number of microparticles that have passed through the through-hole portion. Then, the comparing unit compares the number that has been counted by the counting unit with the stress state information. Here, the stress state information contains the relation information on the relation between the number of microparticles contained in the body fluid and the stress intensity, and therefore, the stress determining unit can determine the stress state of the subject by the comparing unit performing the comparison.

Another characteristic feature of the stress determining device according to the present invention lies in that the device further includes: a life information input unit through which life information on the subject is input; a life information determining unit that determines a stress input level based on the life information; and a learning unit that updates the stress state information on the basis of the life information, wherein the learning unit has a matching degree determining unit that determines the degree of matching between a determination result with respect to the stress input level and a determination result with respect to the stress state and an updating unit that updates the relation information on the basis of the degree of matching that has been determined, and the learning unit learns the stress state information for which the degree of matching is improved even more, by the updating unit repeating the update.

With the above-described configuration, the matching degree determining unit of the learning unit determines the degree of matching between the determination result with respect to the stress input level based on the life information, such as the working environment, and the determination result with respect to the stress state based on the waveform of the ionic current. Furthermore, the updating unit of the learning unit updates the relation information on the basis of the degree of matching. The updating unit repeats the update of the relation information in this manner, and the learning unit thereby learns the stress state information so that the degree of matching between the determination result with respect to the stress input level and the determination result with respect to the stress state improves. Thus, it is possible to provide a stress determining device in which the determination accuracy of the stress determining unit based on the waveform and the stress state information keeps improving.

Advantageous Effects of Invention

It is possible to provide a simple, rapid, and accurate virus measuring method, a virus measuring device, a virus determining program, a stress determining method, and a stress determining device.

BRIEF DESCRIPTION OF DRAWINGS

FIG. 7 is a graph showing a relation between the job, the number of passing particles, and the stress assessment.

FIG. 8 shows a form of a K6 survey sheet.

DESCRIPTION OF EMBODIMENTS

On the basis of the drawings, a stress determining method, a stress determining device that implements the determining method, as well as a virus measuring method, a virus measuring device, and a virus determining program according to embodiments of the present invention will be described.

First Embodiment (Regarding Specimen)

In the present embodiment, a case where tear fluid is used as a body fluid of a subject will be described by way of example. The conjunctival sac (a baglike portion located at the boundary between the eyeball and the lower eyelid) of the subject is flushed with phosphate-buffered saline (hereinafter, referred to simply as "saline"), and the flushing solution containing tear fluid is collected and used as the tear fluid. In the following description, this flushing solution will be referred to as a specimen L1. That is to say, the specimen L1 is saline that contains tear fluid. The specimen L1 is an electrolytic solution, and is capable of conducting ionic current due to salt (sodium chloride). Note that, normally, 7 microliters of tear fluid is always present in the conjunctival sac. In the present embodiment, the conjunctival sac is flushed with 30 microliters of saline.

It is known that herpesvirus may leak into tear fluid of a subject depending on the stress state of the subject. Herpesvirus particles are microparticles with a particle size (diameter) of approximately 200 nanometers. For example, herpes simplex virus 1 (HSV-1 (also abbreviated as "HHV1")) has a particle size of approximately 150 to 180 nanometers. Varicella-zoster virus (VZV (also abbreviated as "HHV3")) has a particle size of approximately 180 to 200 nanometers. Human cytomegalovirus (HCMV (also abbreviated as "HHV5")) has a particle size of approximately 150 to 200 nanometers. Human herpesvirus 6 (HHV-6) has a particle size of approximately 200 nanometers.

A herpesvirus particle has a nucleocapsid composed of a viral DNA, which is located at the center of the microparticle, and a capsid, which is a protein coat that surrounds the viral DNA, and also has an envelope located outside the nucleocapsid, the envelope being made of a lipid bilayer membrane. Glycoproteins called "spikes" project from the surface of the envelope of the herpesvirus particle. These glycoproteins contain amino acids that have negatively charged side chains. Accordingly, herpesvirus particles in the body fluid or saline have a negative surface potential.

In the present embodiment, a case where at least herpes simplex virus 1 is contained as the herpesvirus will be described below by way of example. Also, a case where herpesvirus leaking into tear fluid is used as the stress marker in the subject will be described below by way of example. In the following description, herpesvirus may also be referred to simply as "virus".

(Regarding Stress Determining Device)

Figure 1:
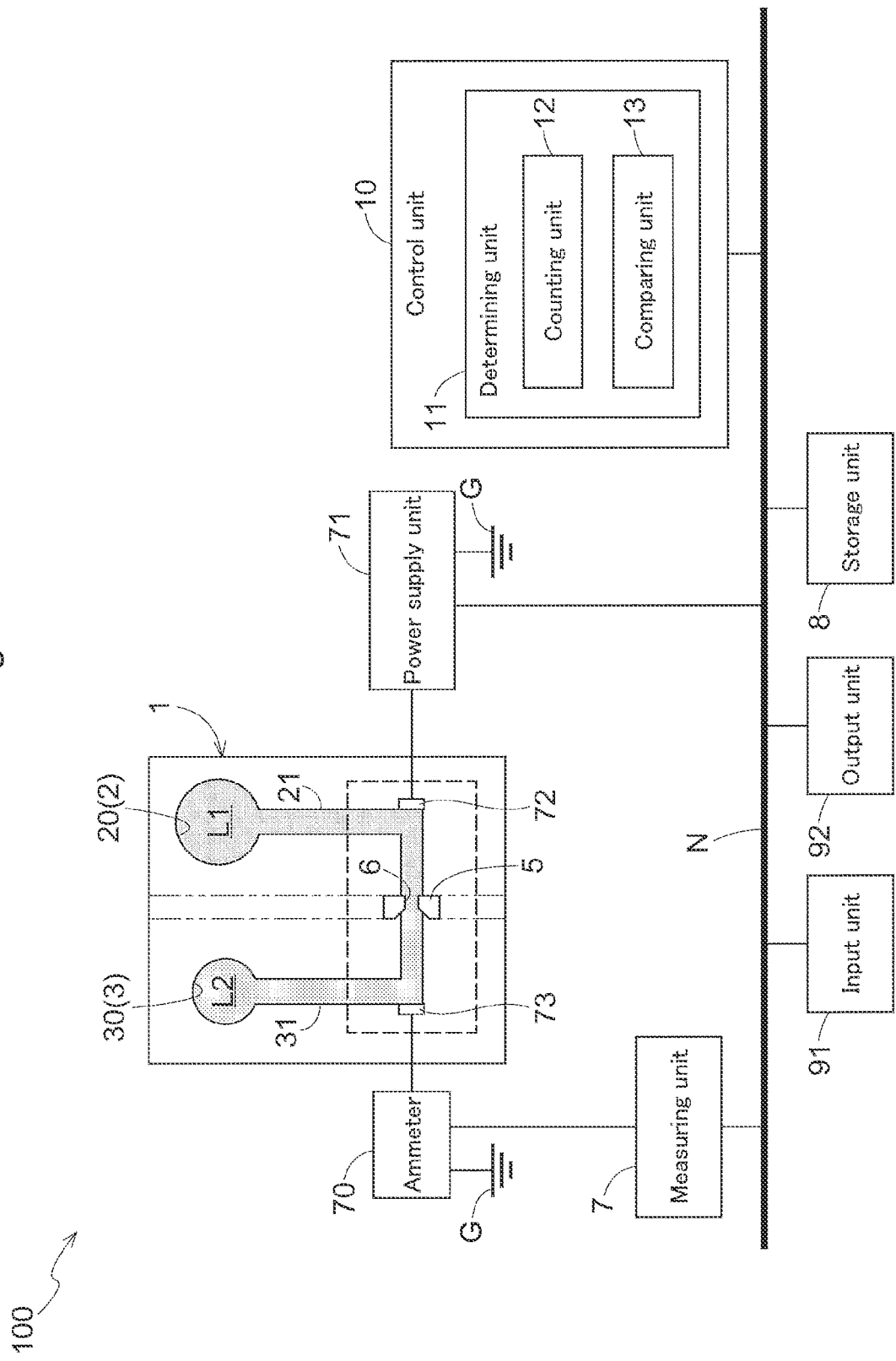
FIG. 1 is a schematic diagram showing the configuration of a determining device of a first embodiment.

FIG. 1 shows the configuration of a determining device 100 that implements a stress determining method according to the present embodiment and that is used as a stress determining device. The determining device 100 includes a test substrate 1 serving as a test chip for a liquid specimen L1 (an example of a liquid specimen) that contains a body fluid of a subject, a measuring unit 7 that obtains information on the waveform of an ionic current from the test substrate 1, a control unit 10, such as a computer, that determines the stress state of the subject on the basis of the information obtained from the test substrate 1, and a power supply unit 71. The measuring unit 7 and other units are connected to the control unit 10 via a network N, such as a data bus or a computer network (a local network or the internet), that enables two-way communication.

The test substrate 1 is a plate-shaped substrate made of an insulating material such as quartz glass or polydimethylsiloxane. The test substrate 1 has a specimen reservoir 2 for storing the specimen L1, an electrolytic solution reservoir 3 for storing an electrolytic solution L2, a separating wall 5 (an example of a separating wall portion) in which a through-hole 6 (an example of a through-hole portion) is formed, a first electrode 72, and a second electrode 73 that is paired with the first electrode 72. The test substrate 1 is used as a test chip for the specimen L1. Note that an electrolytic solution such as saline is used as the electrolytic solution L2. The electrolytic solution L2 is capable of conducting ionic current due to salt (sodium chloride).

The specimen reservoir 2 is a portion that serves as a container for storing the specimen L1. For example, the specimen reservoir 2 is provided as a recess on one side of the test substrate 1. The specimen reservoir 2 has a first circular recess 20 that is a circular recess and serves as the main container for storing the specimen L1 and a first flow channel 21 through which the first circular recess 20 is in communication with the through-hole 6 of the separating wall 5. The first flow channel 21 is connected to one side of the separating wall 5. The first electrode 72 is provided at a location on the first flow channel 21 between the first circular recess 20 and the separating wall 5. The specimen reservoir 2 is filled with the specimen L1. When the specimen reservoir 2 is filled with the specimen L1 without bubbles, electrical continuity is established between the first electrode 72 and the specimen L1. Preferably, a liquid contact surface of the specimen reservoir 2 is surface-treated so as to have hydrophilicity. For example, plasma treatment, UV irradiation, chemical modification, or the like can be used as the surface treatment.

The electrolytic solution reservoir 3 is a portion that serves as a container for storing the electrolytic solution L2. For example, the electrolytic solution reservoir 3 is provided as a recess on the other side of the test substrate 1. The electrolytic solution reservoir 3 has a second circular recess 30 that is a circular recess and serves as the main container for storing the electrolytic solution L2 and a second flow channel 31 through which the second circular recess 30 is in communication with the through-hole 6 of the separating wall 5. The second flow channel 31 is connected to the other side of the separating wall 5, which is the opposite side to the side to which the first flow channel 21 is connected. The second electrode 73 is provided at a location on the second flow channel 31 between the second circular recess 30 and the separating wall 5. The electrolytic solution reservoir 3 is filled with the electrolytic solution L2. When the electrolytic solution reservoir 3 is filled with the electrolytic solution L2 without bubbles, electrical continuity is established between the second electrode 73 and the electrolytic solution L2. Also, the specimen L1 and the electrolytic solution L2 are physically connected to each other via the through-hole 6. When the specimen L1 and the electrolytic solution L2 are physically connected to each other, electrical continuity can be established between the specimen L1 and the electrolytic solution L2.

The first electrode 72 is electrically connected to one end of the power supply unit 71 that is a DC power supply. A predetermined DC voltage (e.g., 0.1 volts) is applied to the first electrode 72 from the power supply unit 71. In the present embodiment, the first electrode 72 is a negative electrode. For example, a silver/silver chloride electrode that is formed by coating the surface of silver with silver chloride can be used as the first electrode 72. In the following description, the voltage applied to the first electrode 72 from the power supply unit 71 may also be referred to simply as the "applied voltage".

The other end of the power supply unit 71 is connected to the ground G. The power supply unit 71 is communicably connected to the control unit 10 via the network N. The power supply unit 71 applies a predetermined voltage according to an instruction from the control unit 10.

The second electrode 73 is an electrode of the opposite polarity to the first electrode 72. In the present embodiment, the second electrode 73 is a positive electrode. The second electrode 73 is electrically connected to an ammeter 70 of the measuring unit 7. A voltage applied from the first electrode 72 generates a DC potential difference between the first electrode 72 and the second electrode 73. As with the first electrode 72, a silver/silver chloride electrode can be used as the second electrode 73. In the following description, the DC potential difference that occurs between the first electrode 72 and the second electrode 73 will be referred to simply as the "potential difference". Virus particles in the specimen L1 migrate (electrophoretically migrate) toward the second electrode 73 along an electric field generated by this potential difference. The voltage applied from the first electrode 72 causes an ionic current to flow between the first electrode 72 and the second electrode 73. This ionic current flows through the through-hole 6.

Figure 2:
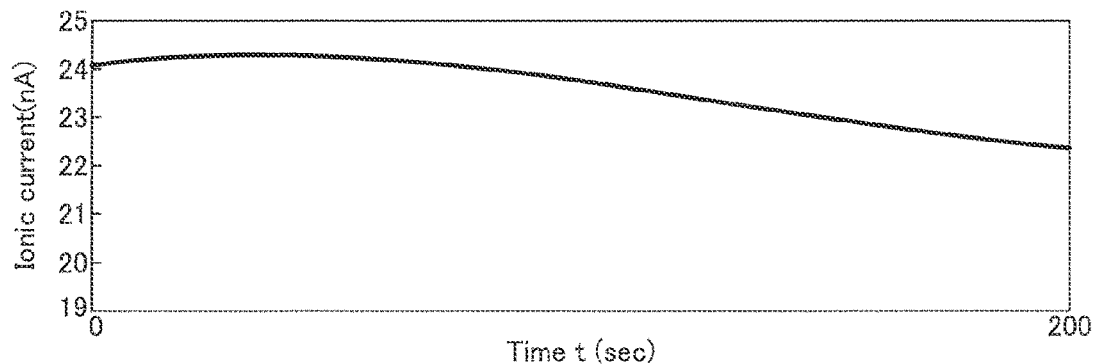
FIG. 2 is a waveform chart in the case where no peak is present.
Figure 3:
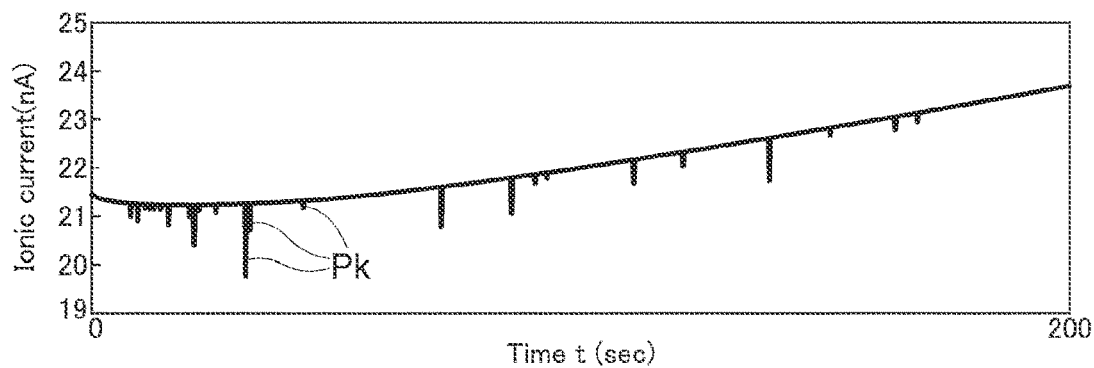
FIG. 3 is a waveform chart in the case where peaks are present.

The measuring unit 7 is a measuring unit that has the ammeter 70 and an interface (not shown) that transmits waveform information on a current value obtained by the ammeter 70 to the control unit 10 via the network N. The ammeter 70 is a measuring instrument that measures a current flowing between the second electrode 73 and the ground G. The ionic current flowing between the first electrode 72 and the second electrode 73 is discharged from the second electrode 73 to the ground G via the ammeter 70. The measuring unit 7 obtains waveform information on the ionic current on the basis of the information on the current value of the ionic current obtained by the ammeter 70, and transmits the waveform information to the control unit 10. In the following description, the waveform information on the ionic current will be referred to simply as the "waveform", and the waveform obtained when the specimen L1 is stored in the specimen reservoir 2 may be referred to particularly as the "waveform of the specimen". FIGS. 2 and 3 show examples of the waveform that represents changes in the current value of the ionic current over time t (sec) when a predetermined voltage is applied from the first electrode 72.

Figure 6:
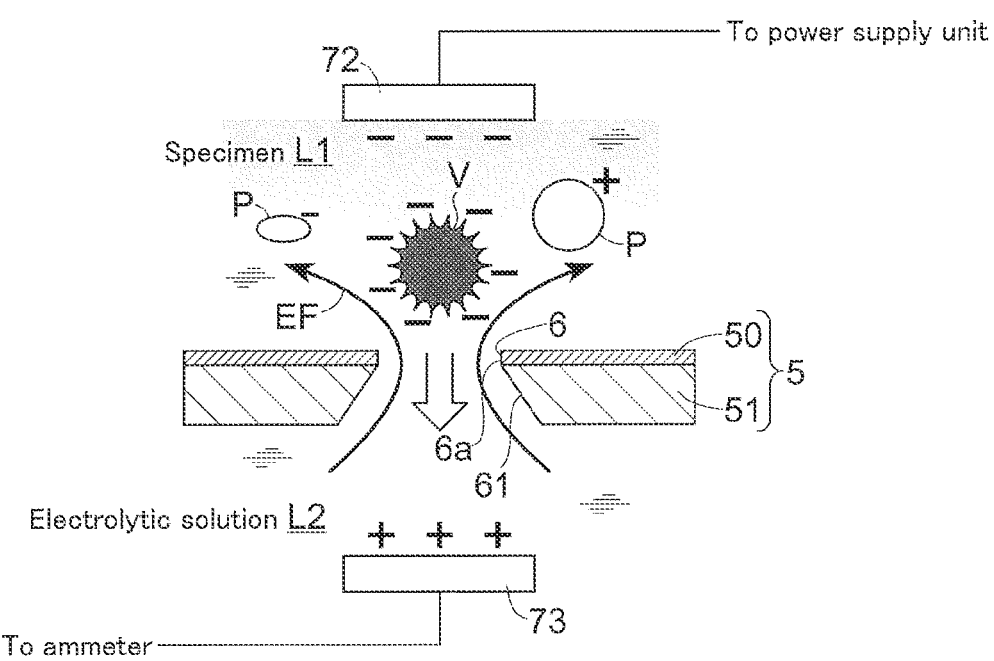
FIG. 6 is an explanatory diagram illustrating the structure of a separating wall and a through-hole and the electrophoresis of virus.

As shown in FIG. 6, the separating wall 5 has a thin plate-shaped (thin film-shaped) substrate 50 made of a solid inorganic oxide of an insulating material such as silicon nitride ($Si_3N_4$), a reinforcing plate 51 that is made of a solid semiconductor such as silicon (Si) and to which the substrate 50 is attached, and the through-hole 6 formed in the substrate 50. The substrate 50 is disposed on the side that is in contact with the first flow channel 21. The substrate 50 may have a thickness of 50 nanometers, for example. The reinforcing plate 51 may have a thickness of 500 micrometers, for example. The separating wall 5 may be obtained by, for example, coating the surface of the reinforcing plate 51 with silicon nitride to form the substrate 50.

The through-hole 6 is a minute pore (solid pore) penetrating the substrate 50, which is a solid. In the present embodiment, the through-hole 6 has a diameter greater than the diameter of a virus particle, and may be, for example, a circular hole (so-called nanopore) having a diameter of 300 nanometers. Note that the through-hole 6 is formed to have a diameter that is greater than the thickness of the substrate 50. In terms of the aspect ratio (ratio of the thickness of the substrate 50 to the diameter of the hole), the through-hole 6 is a low-aspect-ratio nanopore having an aspect ratio of less than 1.

An inner surface 6a of the through-hole 6 is surface-treated so as to have a surface charge of the same polarity as the virus, that is, a negative surface charge. Also, the inner surface 6a is surface-treated so as to have hydrophilicity. For example, the inner surface 6a can be formed using a surface treatment agent that is modified by molecular modification with carbohydrate chains that are present on the surface of a virus to be detected. Since the inner surface 6a has a negative surface charge, the specimen L1 and sodium ions (cations) of the electrolytic solution L2 are attracted to the vicinity of the surface of the inner surface 6a, and an electrical double layer is formed. Note that, in addition to chemical modification such as molecular modification, plasma treatment, UV irradiation treatment, or the like can be used as the surface treatment for making the inner surface 6a hydrophilic.

Note that a window hole 61 that does not block the opening portion of the through-hole 6 and has a greater diameter than the diameter of the through-hole 6 is formed in a portion of the reinforcing plate 51 that corresponds to the through-hole 6. The window hole 61 allows the through-hole 6 to penetrate the separating wall 5.

A method for forming the through-hole 6 will be described. The through-hole 6 can be formed in the following manner: the window hole 61 is formed in a portion of the reinforcing plate 51 through anisotropic etching or the like of silicon using an aqueous potassium hydroxide solution or the like, to thereby make a portion of the substrate 50 that corresponds to the window hole 61 into a silicon nitride membrane, then, a micropore is written on that portion by electron beam lithography or the like, and the written portion is etched by reactive ion etching or the like.

A broad description regarding the waveform of the ionic current and the electrophoresis of virus particles will be additionally given below. As shown in FIG. 6, when a voltage is applied to the first electrode 72, a potential difference is generated and causes a virus particle V in the specimen L1 to migrate toward the second electrode 73 due to electrophoresis. As a result of this migration, the virus particle V passes through the through-hole 6.

In addition, the potential difference generated by applying the voltage to the first electrode 72 induces an electroosmotic flow EF in the vicinity of the inner side of the electrical double layer of the inner surface 6a. Since the inner surface 6a has a negative surface charge, which is of the same polarity as the virus, the flow direction of the electroosmotic flow EF is opposite to the migrating direction of the virus particle V. This an electroosmotic flow EF inhibits impurity microparticles P (e.g., microparticles of proteins or the like) that have a lower negative surface charge than the virus particle V from migrating in the migrating direction of the virus particle V. Therefore, the impurity microparticles P cannot pass through the through-hole 6. As a result, the impurity microparticles P are separated from the virus particle V, and the virus particle V selectively passes through the through-hole 6 (an example of a separation step).

In addition, when a voltage is applied to the first electrode 72, an ionic current flows between the first electrode 72 and the second electrode 73. The current value of this ionic current depends on the concentrations of the specimen L1 and the electrolyte (sodium chloride) in the electrolytic solution L2, as well as the cross-sectional area, of a cross section intersecting the axial direction of the through-hole 6, of an electrolytic solution (the specimen L1 or the electrolytic solution L2 and a mixture of these) that is present in the through-hole 6. For this reason, if a microparticle such as a virus particle enters the through-hole 6, the ionic current flowing through the through-hole 6 decreases, because the microparticle displaces the electrolytic solution in the through-hole 6. More specifically, each time a virus particle passes through the through-hole 6, a peak Pk appears in the waveform of the ionic current flowing between the first electrode 72 and the second electrode 73, the peak Pk being a single spike-like waveform that represents a decrease in the current value (see FIG. 3). Therefore, if the number of peaks Pk that are detected per unit time is counted, the number of virus particles that have passed through the through-hole 6 per unit time (hereinafter, the number of virus particles that have passed through the through-hole 6 may also be referred to simply as the "number of passing particles") can be measured. In the case of FIG. 3, 18 peaks Pk are detected during a measurement time of 200 seconds, and the number of passing particles is thus determined to be 18. Note that, if no microparticle such as a virus particle is present in the specimen L1, no peak Pk appears in the waveform of the ionic current (see FIG. 2). In this manner, the determining device 100 is capable of detecting each single virus particle with high sensitivity.

Figure 4:
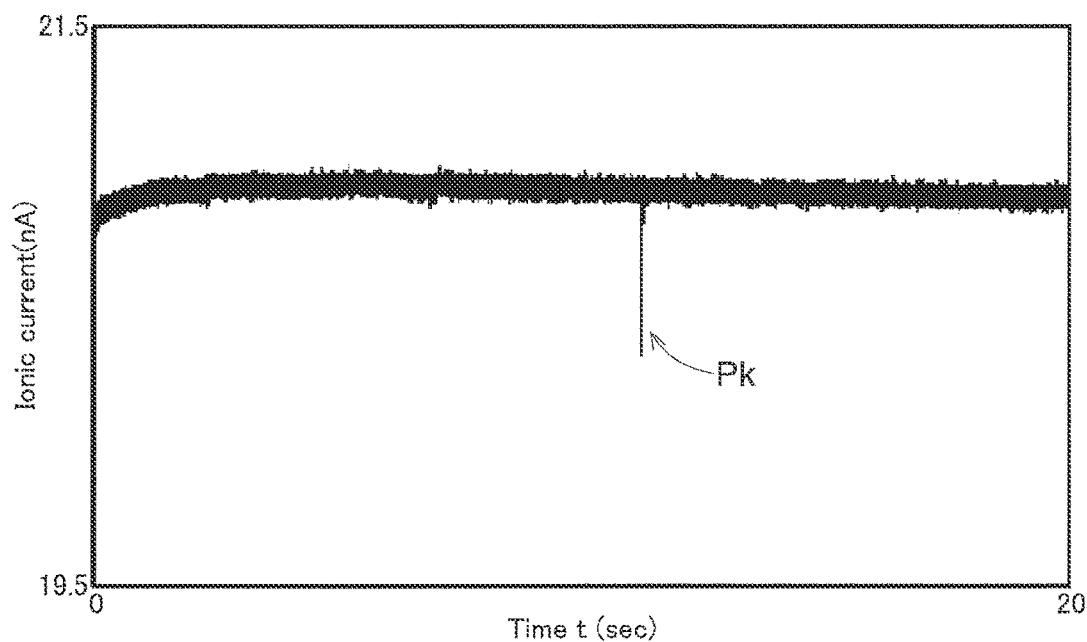
FIG. 4 is a waveform chart showing an example of a peak.
Figure 5:
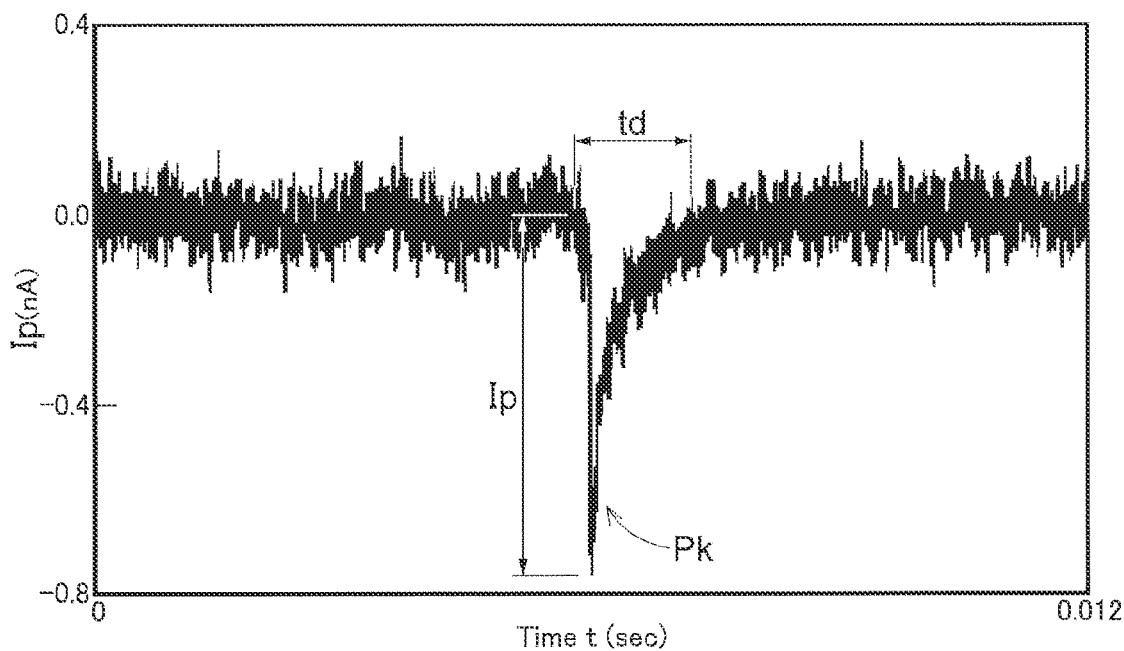
FIG. 5 is an explanatory diagram of a peak shape.

FIG. 4 shows a peak Pk that appears when a herpes simplex virus 1 (HSV-1) particle passes through the through-hole 6. FIG. 5 is an enlarged view of the peak Pk in FIG. 4. As shown in FIG. 5, the peak Pk has a predetermined pulse height Ip and a predetermined pulse width td. The pulse height Ip is the difference between the peak start or the peak end and the peak top, of the peak Pk. The pulse width td is the time that has elapsed between the peak start and the peak end, of the peak Pk. The shape of the peak Pk, such as the pulse height Ip and the pulse width td, varies depending on the kind of virus (the viral species and the state (activity) of the virus, or more specifically, the particle size of the virus, the type of glycoprotein on the surface of the envelope, and the like).

Here, the concept of the kind of virus in the present embodiment includes the viral species, that is, the "family", such as the difference between herpesvirus and influenza virus, and the "type", such as the difference between herpes simplex virus 1 and human herpesvirus 6, as well as the difference in the "activity (state)" between viruses of the same kind or the same type. The concept of activity includes the so-called viability of the virus, for example, a state in which the virus is active/infectious (referred to as "viable", "infectious virus", or the like) and a state in which the virus is inactivated/is no longer infectious (referred to as "non-viable", "inviable", "non-infectious", or the like). In the following description, a virus in the active/infectious state will be referred to simply as "active virus" or the like. Moreover, a virus in the inactivated/no-longer-infectious state will be referred to simply as "inactive virus" or the like. Note that an active virus and an inactive virus have different surface potentials (for example, herpesviruses lose their activity if the envelopes are destroyed) for the reason that the state of the particle surface is different, or other reasons. Therefore, an active virus and an inactive virus cause different peaks Pk.

The control unit 10 is a functional unit that controls the entire determining device 100. The control unit 10 of the present embodiment is implemented by means of software on a computer (a personal computer in the present embodiment; hereinafter referred to simply as "CPU") that includes at least a central processing unit and a temporary memory. The control unit 10 receives input of information from an input unit 91 (an example of a life information input unit) that is connected to the CPU and is an input interface, such as a keyboard or a mouse, through which information is input, and outputs various kinds of internally processed information from an output unit 92 that is an output interface, such as a monitor, a speaker, or a printer, through which information is output. The software (program) that implements the control unit 10 and the various kinds of information, such as the information that is input from the input unit 91, the information that is to be output from the output unit 92, and stress state information that is to be internally processed by the control unit 10, are stored in a storage unit 8 that is a storage device or a storage medium. The input unit 91, the output unit 92, and the storage unit 8 are communicably connected via the network N. Examples of the storage unit 8 include, but are not limited to, a magnetic storage medium such as a hard disk, an optical disk such as a CD or a DVD, an SSD, a USB memory, and a flash memory such as a memory card, as well as a cloud server and a rental server.

As shown in FIG. 1, the control unit 10 has a determining unit 11 (an example of a stress determining unit) that is implemented by software. The determining unit 11 is a functional unit that determines the stress state of the subject by comparing the waveform obtained from the measuring unit 7 with the stress state information read from the storage unit 8. The determining unit 11 has a counting unit 12 that counts, on the basis of the waveform, the number of virus particles contained in the specimen L1 that have passed through the through-hole 6 due to electrophoresis per unit time (the number of passing particles), and a comparing unit 13 that compares the number of passing particles with the stress state information.

The stress state information contains information (hereinafter referred to simply as the "relation information") on the relation between waveforms of specimens that are obtained under predetermined conditions and stress states (e.g., the kind and the intensity of stress) of humans (e.g., subjects). In the present embodiment, the stress state information contains at least relation information on the relation between the numbers of peaks Pk in waveforms of specimens obtained under predetermined measurement conditions and the intensities of stress. Note that, for example, the value of the applied voltage, the measurement time (the time period for which the voltage is applied and counting is continued), the concentrations of the specimen L1 and the electrolyte in the electrolytic solution L2, the structure of the test substrate 1, and the like may be provided as the predetermined measurement conditions. The following description assumes that the predetermined measurement conditions are fulfilled.

Table 1 shows an example of the relation information. This relation information contains information on the ranges of the number of passing particles per unit time, or 5 minutes, levels (S1 to S5) of stress intensity that correspond to these ranges, and jobs corresponding to the respective levels of stress intensity. With regard to the jobs, a case is shown by way of example in which the nurse (after a day shift), the nurse (after a night shift), the ward head nurse, the ward clerk, and the ward pharmacist, which are jobs in hospital wards, are used as the jobs corresponding to the respective levels of stress intensity. Specifically, the following five levels, a nurse (after a day shift) level (low stress), a nurse (after a night shift) level (somewhat low stress), a ward head nurse level (moderate stress), a ward clerk level (somewhat high stress), and a ward pharmacist level (high stress) are assigned to the respective levels S1 to S5 in that order. Note that the stress intensity levels increase in ascending order from the level S1 to the level S5. Also, both the significance of duties (causes of mental stress in particular) and the length of working hours (causes of physical stress in particular) required by these jobs increase in the order of the nurse (after a day shift), the nurse (after a night shift), the ward head nurse, the ward clerk, and the ward pharmacist. Note that such relation information can be created beforehand by obtaining the number of passing particles and the stress intensity with respect to a plurality of subjects.

TABLE 1

| Stress intensity | S1 | S2 | S3 | S4 | S5 |
| --- | --- | --- | --- | --- | --- |
| Ranges of number of passing particles (particles/5 min.) | At most 5 | From 5 to 10 | From 11 to 15 | From 16 to 20 | At least 21 |
| Corresponding job indications | Nurse (after a day shift) level | Nurse (after a night shift) level | Ward head nurse level | Ward clerk level | Ward pharmacist level |
| Replaced indications | Low stress | Somewhat low stress | Moderate stress | Somewhat high stress | High stress |

The relation information shown in Table 1 will be described using examples. If the number of passing particles is 17, the corresponding stress intensity level is the level S4. Also, the corresponding job is the ward clerk. If the number of passing particles is 11, the corresponding stress intensity level is the level S3. Also, the corresponding job is the ward head nurse.

The counting unit 12 measures the number of peaks Pk, which is regarded as the number of passing particles, in a waveform obtained within a predetermined period of time (e.g., a short period of time of about 5 minutes) in a state in which a voltage is applied to the first electrode 72, and counts the number of passing particles. Note that, if the pulse height Ip of a peak Pk is less than a predetermined value (e.g., less than 0.05 nanoamperes), the counting unit 12 excludes this peak from the measurement target.

The comparing unit 13 compares the number of passing particles counted by the counting unit 12 with the stress state information read from the storage unit 8, and determines the stress intensity level corresponding to the number of passing particles. For example, if the number of passing particles counted by the counting unit 12 is 17, the comparing unit 13 determines that the stress intensity level is the level S4. If the number of passing particles is 11, the comparing unit 13 determines that the stress intensity level is the level S3. In this manner, the determining unit 11 determines stress of the subject.

(A Series of Steps for Determining Stress)

The following is a description of a series of steps for determining stress. A measurer or the like stores the specimen L1 in the specimen reservoir 2 and also stores the electrolytic solution L2 in the electrolytic solution reservoir 3. Then, the specimen L1 and the electrolytic solution L2 are brought into contact with each other via the through-hole 6 so that electricity can flow therebetween (a contact step).

After putting the specimen L1 and the electrolytic solution L2 into a state in which electricity can flow therebetween, the measurer or the like inputs measurement conditions (e.g., the measurement time and the applied voltage) and an instruction to start the measurement to the control unit 10 via the input unit 91. Then, the control unit 10 instructs the power supply unit 71 to apply voltage under conditions corresponding to the input measurement conditions. According to the instruction, the power supply unit 71 applies a voltage to the first electrode 72 under predetermined conditions.

When a predetermined voltage is applied to the first electrode 72, virus particles in the specimen L1 migrate toward the second electrode 73 due to electrophoresis. During this migration, when a virus particle passes through the through-hole 6, a peak Pk appears in the waveform of the ionic current (a current measuring step and a passing step). The counting unit 12 counts the number of peaks Pk as the number of passing particles (a determining step and a counting step).

On the basis of the number of passing particles and the relation information, the comparing unit 13 determines the corresponding stress intensity (a stress determining step and a comparing step). The control unit 10 obtains the determination result from the determining unit 11 and outputs the determination result from the output unit 92 (for example, displays the determination result on the monitor). During this output, the control unit 10, on the basis of the determination result obtained from the determining unit 11 and the relation information, replaces the determination result with a term by which the stress state can be intuitively understood, and outputs the term from the output unit 92. For example, if the determination result is the level S1, "low stress" is indicated by the output unit 92. As a result of this replacement, a user can intuitively understand the stress level.

Example 1

FIG. 7 shows the numbers of passing particles (vertical axis) obtained by measuring specimens L1 of respective subjects having various jobs in a hospital ward. The numbers of passing particles shown are the values obtained by performing measurement for 5 minutes. Five types of jobs, the nurse (after a day shift), the nurse (after a night shift), the ward head nurse, the ward clerk, and the ward pharmacist are shown by way of example. In FIG. 7, the individual jobs are plotted as a solid circle, a hollow circle, a solid square, a hollow square, or a solid triangle, in the order of the nurse (after a day shift) to the ward pharmacist. Hereinafter, determination of stress of the subjects corresponding to these plotted points using the stress determining method and the determining device 100 according to the present embodiment will be described.

The determining unit 11 determines the intensity of stress of the subjects corresponding to the respective plotted points, on the basis of the numbers of passing particles and the relation information shown in Table 1. In the case shown in FIG. 7, the stress intensity levels of the subjects are determined as the level S1, the level S2, the level S3, the level S4, or the level S5 in the order of all the nurses (after a day shift), the nurse (after a night shift), the ward head nurse, the ward clerk, and the ward pharmacist.

After the control unit 10 has obtained the determination results from the determining unit 11, the control unit 10 replaces the determination results, such as the level S1, with terms by which the stress state can be intuitively understood, and outputs the terms from the output unit 92. In the example shown in FIG. 7, the determination results with respect to the respective plotted points for the nurses (after a day shift), the nurse (after a night shift), the ward head nurse, the ward clerk, and the ward pharmacist are individually replaced with the terms "low stress", "somewhat low stress", "moderate stress", "somewhat high stress", and "high stress", in that order, and are output from the output unit 92 or the like. In the case of the present example, the determination results match the jobs of the subjects. More specifically, the determination results obtained using the stress determining method according to the present embodiment match the significance of duties, and the length of working hours, required by the jobs of these subjects. In this manner, with the stress determining method according to the present embodiment, it is possible to make an assessment highly correlated with the duties and the working hours required by the job of a subject.

COMPARATIVE EXAMPLE

FIG. 7 shows, in addition to the numbers of passing particles, the scores (horizontal axis) of a questionnaire assessment of stress of the individual subjects having the respective jobs in the hospital ward. The questionnaire assessment of stress was administered using a K6 survey sheet (see FIG. 8) corresponding to the mood or anxiety disorder survey sheet disclosed in Non-Patent Document 1. The stress assessment scores (hereinafter, referred to simply as "scores") are interpreted such that the higher the value of a score is, the higher the self-reported stress level is.

On the basis of the K6 survey sheet, the higher the stress assessment score is, the higher the stress of the relevant subject is. However, in the example shown in FIG. 7, there is no noteworthy correlation between the stress assessment scores and the duties and the working hours required by the jobs of the subjects. When, for example, the nurses (after a day shift) are focused on, the stress assessment scores differ significantly among the individual subjects even though their duties and working hours are similar.

As described above, with the determining device 100 according to the present embodiment, it is possible to make a simple and rapid assessment that is highly correlated with the type and the level of external factors of stress, such as the duties and the working hours required by the job of a subject, compared with a conventional questionnaire assessment.

Second Embodiment

Figure 9:
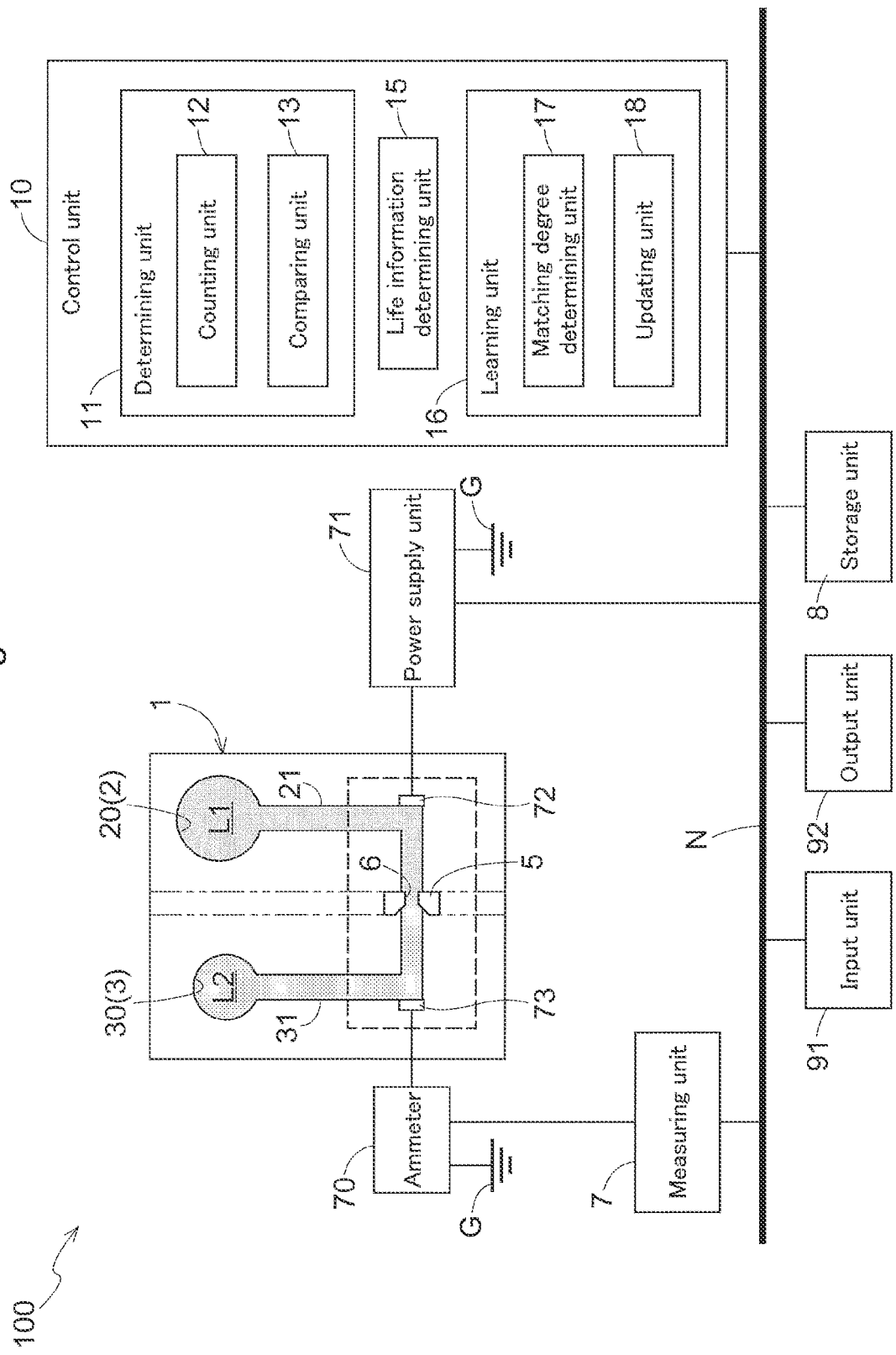
FIG. 9 is a schematic diagram showing the configuration of a determining device of a second embodiment.

In the determining device 100 according to the first embodiment, the control unit 10 has the determining unit 11. A determining device 100 of a second embodiment is different in that, as shown in FIG. 9, the control unit 10 further has a life information determining unit and a learning unit 16 that are implemented by means of software, in addition to the determining unit 11. Also, the determining device 100 according to the first embodiment has the stress state information in the form of the relation information shown in Table 1. The determining device 100 of the second embodiment is different in having, in addition to the relation information shown in table 1, first relation information shown in Table 2 and second relation information in the form that contains a function such as that shown in FIG. 10, as the stress state information, the first and the second relation information being stored in the storage unit 8. Otherwise, the determining device 100 of the second embodiment is the same as the determining device 100 of the first embodiment. Similarities with the first embodiment will not be described below.

TABLE 2

| Life information | Nurse (after a day shift) | Nurse (after a night shift) | Ward head nurse | Ward clerk | Ward pharmacist |
|---|---|---|---|---|---|
| Stress input level | C1 | C2 | C3 | C4 | C5 |

Example 2

Figure 10:
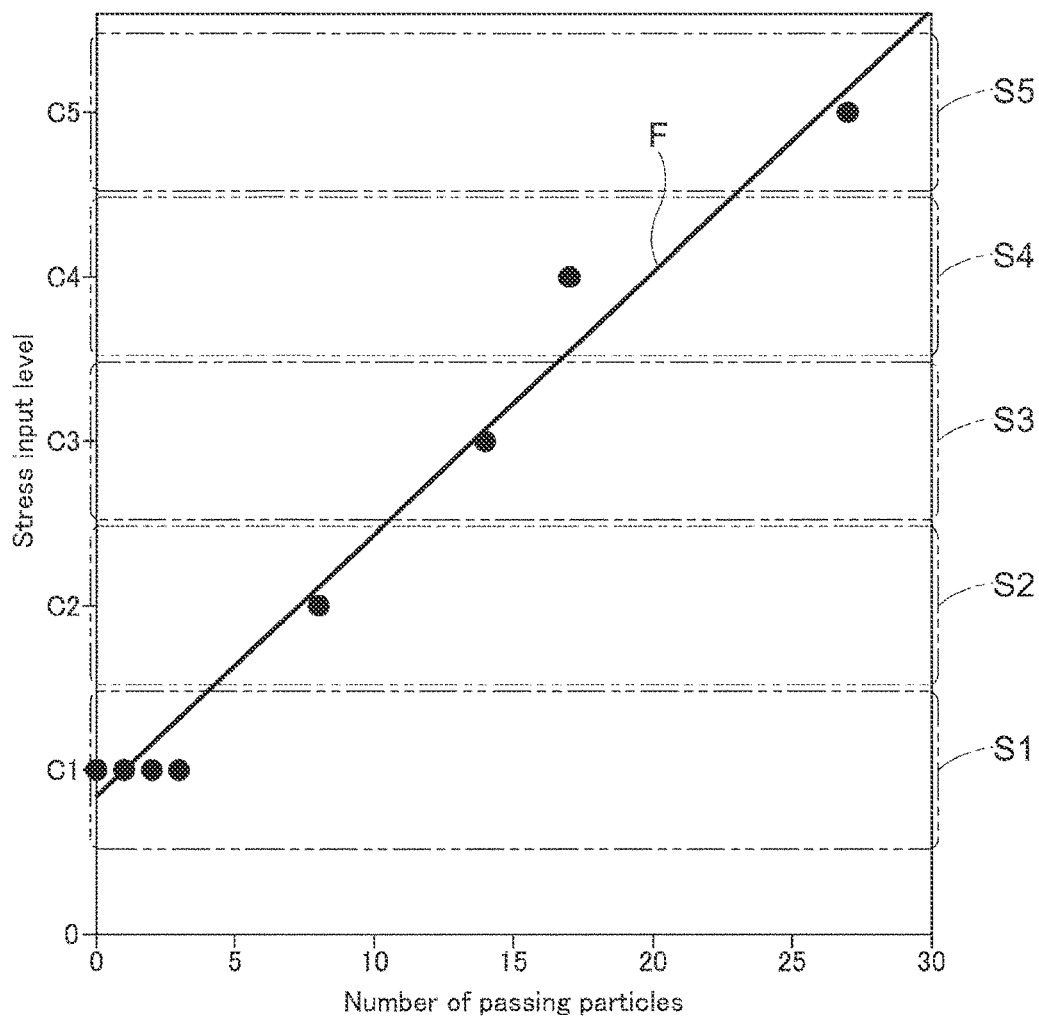
FIG. 10 is a graph showing a relation between the stress input level and the number of passing microparticles.

The second relation information shown in FIG. 10 contains intersections (plotted points indicated by solid circles) of the stress input levels (vertical axis) of stress of subjects that have been input in the past and the numbers of passing particles (horizontal axis), a function F obtained by approximating the plot with a predetermined regression equation (a linear function, in the case of FIG. 10) based on the least-squares method, as well as stress intensity range information on the stress intensity ranges (levels 51 to S5) corresponding to the values of the function F. The stress input levels will be described later. Table 3 shows raw values of the plotted points in FIG. 10. Note that the second relation information is not limited to a regression equation based on the least-squares method, and can be created using a learning method that minimizes error by using teacher data.

TABLE 3

| Subject No. | Job | Number of passing particles | Stress input level |
|---|---|---|---|
| 1 | Nurse (after a day shift) | 0 | C1 |
| 2 | Nurse (after a day shift) | 0 | C1 |
| 3 | Nurse (after a day shift) | 0 | C1 |
| 4 | Nurse (after a day shift) | 0 | C1 |
| 5 | Nurse (after a day shift) | 1 | C1 |
| 6 | Nurse (after a day shift) | 2 | C1 |
| 7 | Nurse (after a day shift) | 3 | C1 |
| 8 | Nurse (after a day shift) | 3 | C1 |
| 9 | Nurse (after a night shift) | 8 | C2 |
| 10 | Ward head nurse | 14 | C3 |

TABLE 3-continued

| Subject No. | Job | Number of passing particles | Stress input level |
|---|---|---|---|
| 11 | Ward clerk | 17 | C4 |
| 12 | Ward pharmacist | 27 | C5 |

The stress input levels of the present embodiment are classes into which external factors of stress, which are estimated from the life information of subjects, are divided according to the severity of stress experienced by the subjects. In the present embodiment, the five types of jobs, that is, the nurse (after a day shift), the nurse (after a night shift), the ward head nurse, the ward clerk, and the ward pharmacist, are regarded as being external factors of stress, and categorized into the stress input levels (C1 to C5). Also, the life information of the present embodiment means factors that can cause stress, such as, for example, the job of a subject, the type of work and the role at work, as well as the time of day worked and the working hours. For example, a nurse who takes care of a larger number of patients has more duties and feels a higher level of stress. Similarly, a night shift worker bears a greater physical burden than a day shift worker. In this case, the life information is the job, and the stress input level is the severity of external stress that is estimated from the job.

The life information determining unit 15 shown in FIG. 9 is a functional unit that determines the stress input level on the basis of the life information of the subject that is input from the input unit 91 or the like. The life information determining unit 15 reads and references the first relation information shown in Table 2 from the storage unit 8, thereby determining the stress input level. For example, if the job, which is the life information, of the subject is the ward clerk, the life information determining unit 15 determines that the stress input level is the level S4.

The comparing unit 13 of the determining unit 11 substitutes the number of passing particles counted by the counting unit 12 into the function F (see FIG. 10) of the stress state information read from the storage unit 8, and determines the stress intensity level corresponding to the number of passing particles. For example, if the number of passing particles counted by the counting unit 12 is 21, the value of the function is about 4.2. This value is within the range of the level S4, and therefore, the comparing unit 13 determines that the stress intensity level is the level S4. Similarly, if the number of passing particles is 6, the comparing unit 13 determines that the stress intensity level is the level S2. In this manner, the determining unit 11 determines stress of the subject.

The learning unit 16 is a functional unit that learns stress state information that increases the degree of matching between the determination result with respect to the stress input level and the determination result with respect to the stress state even more. The learning unit 16 has a matching degree determining unit 17 that determines the degree of matching between the determination result with respect to the stress input level and the determination result with respect to the stress state, and an updating unit 18 that updates the second relation information on the basis of the degree of matching. As a result of the updating unit 18 repeating the update, the learning unit 16 learns stress state information that increases the degree of matching with the determination result with respect to the stress state even more.

The matching degree determining unit 17 is a functional unit that determines the degree of matching between the determination result with respect to the stress input level, which is determined by the life information determining unit 15, and the determination result with respect to the stress state, which is determined by the determining unit 11. For example, if the determination result with respect to the stress input level is the same as the determination result with respect to the stress state, it is determined that they match with each other. If not, it is determined that they do not match with each other.

The updating unit 18 is a functional unit that updates the second relation information on the basis of the degree of matching determined by the matching degree determining unit 17. If the matching degree determining unit 17 determines that the determination results match with each other, the updating unit 18 updates the second relation information. During this update, the updating unit 18 adds the determined number of passing particles and stress input level of the subject to the second relation information and updates the function F. This update improves the probability of the matching degree determining unit 17 determining that the determination results match with each other in subsequent stress determinations. That is to say, in subsequent stress determinations, the degree of matching between the determination result with respect to the stress state and the determination result with respect to the stress input level increases even more.

The updating unit 18 updates the second relation information even if the matching degree determining unit 17 determines that the determination results do not match with each other. Preferably, the content of this update is weighted relative to that in the case where the matching degree determining unit 17 determines that the determination results match with each other. For example, when approximating the second relation information using the least-squares method, it is possible to reduce the weight of the mismatching data relative to that of the matching data. This update improves the probability of the matching degree determining unit 17 determining that the determination results match with each other in subsequent stress determinations. That is to say, in subsequent stress determinations, the degree of matching between the determination result with respect to the stress state and the determination result with respect to the stress input level increases even more.

After updating the second relation information, the updating unit 18 instructs the determining unit 11 to perform a second determination based on the new function F. The control unit 10 obtains the result of the second determination from the determining unit 11 and outputs this second determination result from the output unit 92. The statistical reliability of the value of the second determination result increases as the number of data items increases.

The updating unit 18 repeats the above-described update each time a stress determination is performed. Thus, in the determining device 100, the degree of matching between the determination result with respect to the stress state and the determination result with respect to the stress input level improves each time a stress determination is performed, and stress determination that reflects the actual stress state can be achieved.

Third Embodiment

The determining unit 11 of the determining device 100 according to the first embodiment determines (identifies) the kind of a virus contained in the specimen L1 and can also be used to identify a disease in the subject on the basis of the determined kind of virus, to facilitate the diagnosis and treatment of a disease by a doctor. That is to say, a determining device 100 of a third embodiment is used as a virus measuring device.

Figure 12:
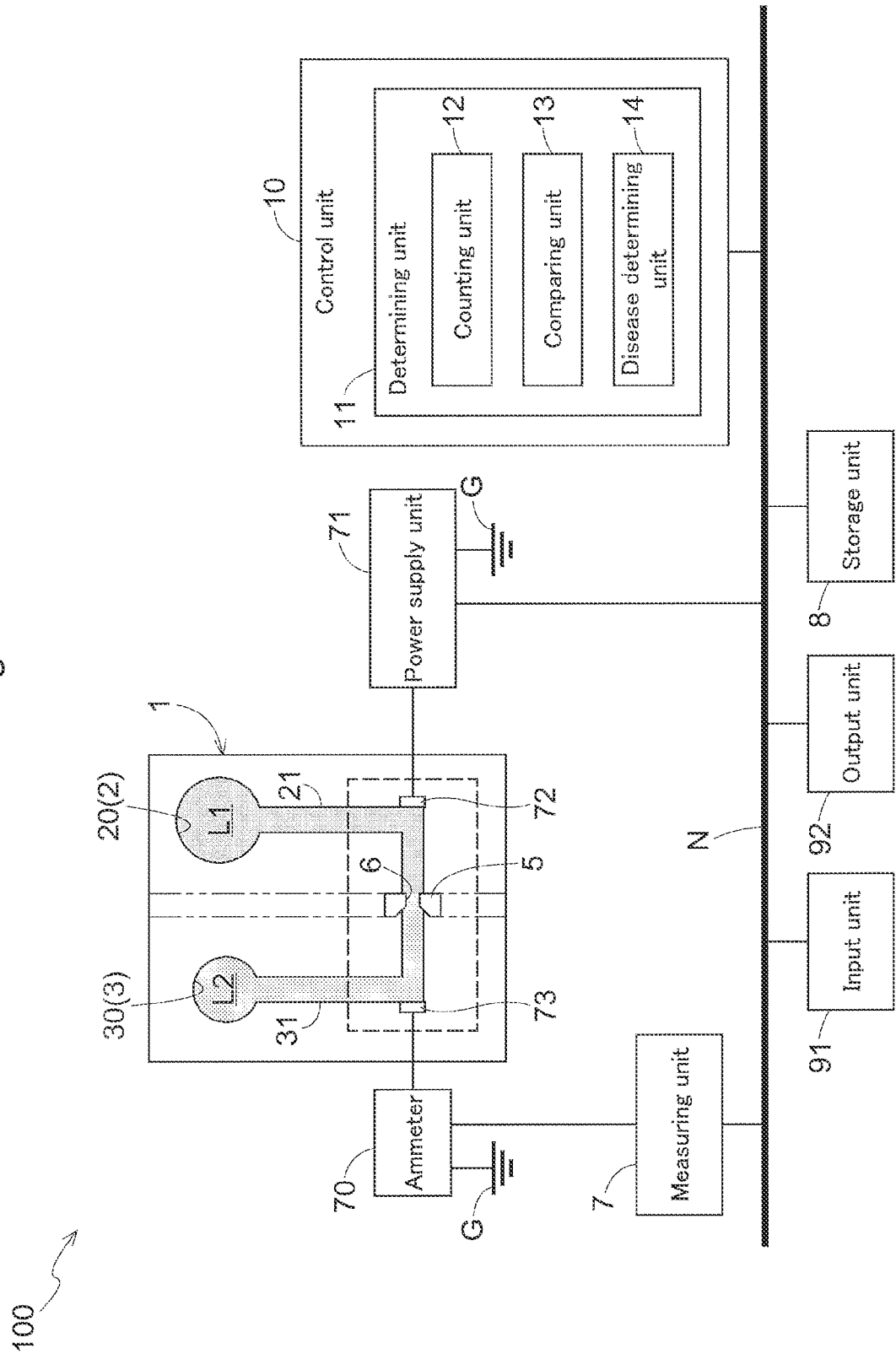
FIG. 12 is a schematic diagram showing the configuration of a measuring device of a third embodiment.

Hereinafter, the components, operations, and effects that are different from those of the first embodiment will be mainly described. FIG. 12 shows the configuration of the determining device 100 according to the third embodiment.

The determining unit 11 has a disease determining unit 14, in addition to the counting unit 12 and the comparing unit 13 (an example of a virus determining unit).

In the first embodiment, the comparing unit 13 compares the number of passing particles counted by the counting unit 12 with the stress state information read from the storage unit 8, and determines the stress intensity level corresponding to the number of passing particles. Instead, the comparing unit 13 of the third embodiment determines, on the basis of a peak Pk corresponding to a trigger sent by the counting unit 12 as will be described later and waveform information that will be described later, the kind of a virus that causes the peak Pk.

In the first embodiment, the counting unit 12 measures the number of peaks Pk, which is regarded as the number of passing particles, in a waveform obtained within a predetermined period of time in a state in which a voltage is applied to the first electrode 72, and counts the number of passing particles. Instead, the counting unit 12 of the third embodiment determines the presence of a peak Pk in a waveform obtained within a predetermined period of time in a state in which a voltage is applied to the first electrode 72, and counts the number of passing particles, and when the presence of a peak Pk is identified, the counting unit 12 sends the comparing unit 13 an instruction (hereinafter, referred to as the "trigger") to determine the kind of virus, as will be described later, and furthermore counts the kinds of viruses determined by the comparing unit 13 and the number of virus particles. As will be described later, the comparing unit 13 completes the determination of the kind of virus within at most 10 minutes. The determination result of the comparing unit 13 is output from the output unit 92.

The disease determining unit 14 determines a disease in the subject on the basis of the kinds of viruses determined by the comparing unit 13, the number of virus particles for each kind of virus, and disease information that will be described later. Details of the determination of a disease will be described later. The determination result of the disease determining unit 14 is output from the output unit 92. The determination of a disease in the present embodiment and the concept thereof include not only determination of the name of the disease (disease name) but also determination of information (e.g., information regarding the viral activity) that is needed to decide the treatment policy (e.g., prescription of medication).

The storage unit 8 stores, instead of, or in addition to, the stress state information, the waveform information on the peaks Pk (see FIG. 5, etc.) corresponding to known viruses and the disease information corresponding to known viruses.

The waveform information is a database that contains information regarding the shapes of the peaks Pk corresponding to known viruses. The waveform information contains information with which the kinds of viruses corresponding to individual peaks Pk in the waveform obtained from the measuring unit 7 can be determined by comparing the individual peaks Pk in the waveform obtained from the measuring unit 7 with the information.

Figure 13:
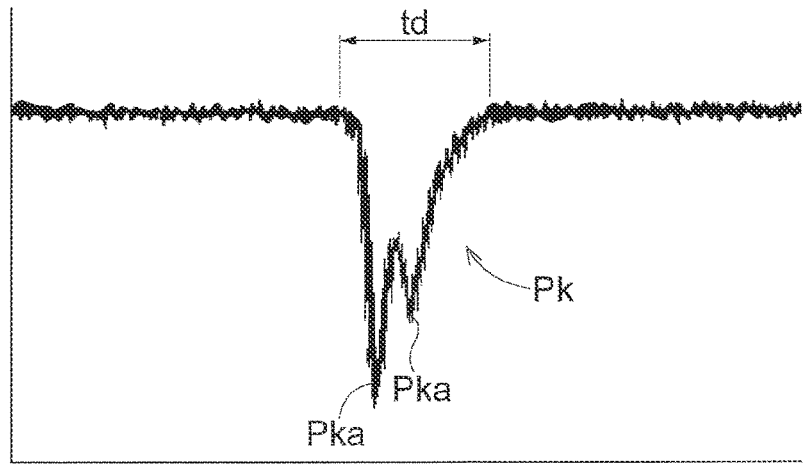
FIG. 13 shows an example of the peak shape.
Figure 14:
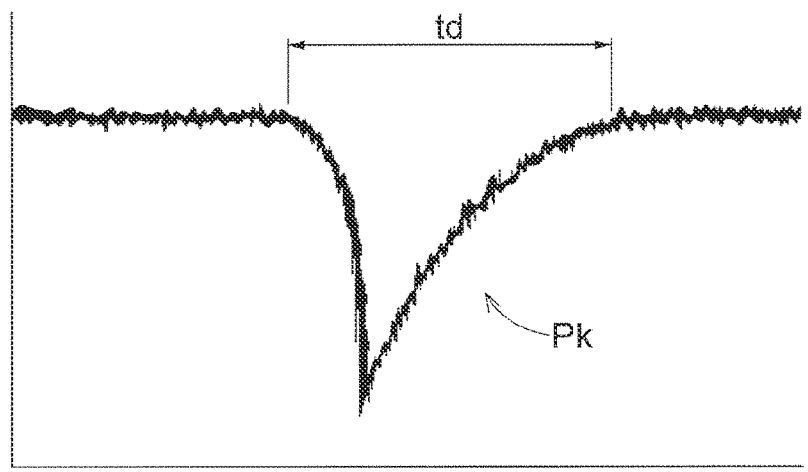
FIG. 14 shows an example of the peak shape.
Figure 15:
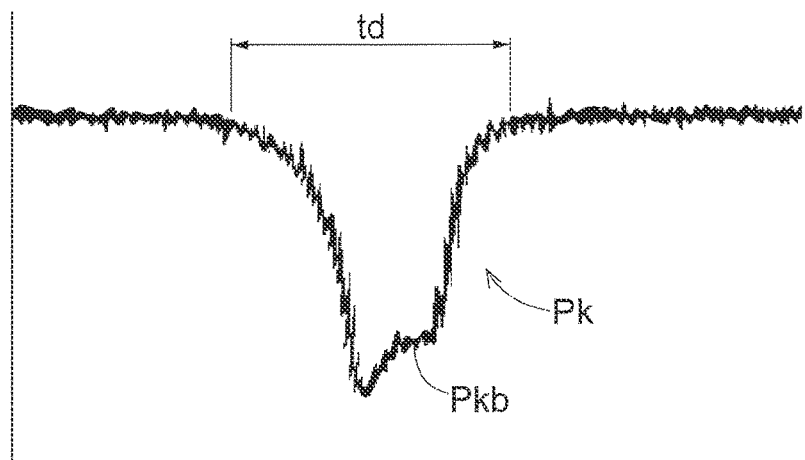
FIG. 15 shows an example of the peak shape.

FIGS. 13 to 15 show the shapes (waveforms) of peaks Pk by way of example. The waveform in FIG. 13 shows a case by way of example in which there is a single peak Pk as a whole, but the peak Pk has a plurality of (e.g., two) sub-peaks Pka that can be observed separately (the peak has split). Note that, although FIG. 13 shows the two sub-peaks Pka with different pulse heights and pulse widths, sub-peaks Pka may also have substantially equal pulse heights or pulse widths. The waveform in FIG. 14 shows a case by way of example in which there is a broad peak Pk, especially, tailing. Another example of the broad peak Pk may be fronting, which is not shown. The waveform in FIG. 15 shows a case by way of example in which there is a shoulder peak Pkb in a portion of a peak Pk. There may be cases where a plurality of shoulder peaks Pkb occur.

The waveform information of the present embodiment may be, for example, a learning model (an example of a learned model; hereinafter, referred to simply as the "learned model") that is created beforehand through leaning using a machine learning technique such as deep learning. The waveform information of the present embodiment is obtained by preparing a plurality of different known viruses of different families, types, or activity levels beforehand, and repeatedly obtaining peaks Pk that appear when virus particles of these known viruses pass through the through-hole 6 as teacher data, thereby performing tuning (reinforcement), and makes it possible that, when a peak Pk caused by a certain kind of virus (e.g., active herpes simplex virus 1) is input, the kind of virus can be determined with a sufficiently high probability (e.g., a probability of at least 99%). In other words, when the learned model is used, the comparing unit 13 can determine the kind of virus with a sufficiently high probability by merely obtaining a single pulse.

When creating the waveform information through learning, it is possible to perform learning focusing on a feature value of peaks Pk. For example, the above-described pulse height Ip, pulse width td, tailing, fronting, shoulder peak Pkb, or the like may be used as the feature value, or the number of sub-peaks Pka or the pulse height and pulse width of each sub-peak Pka may be used. Also, when creating the waveform information through learning, features of the shapes of peaks Pk may be extracted by convolution and pooling and used for learning.

The disease information is a database that contains information for identifying diseases on the basis of the kinds of viruses and the counted numbers of virus particles. The disease information contains information with which a disease can be identified on the basis of the kinds of viruses and the number of passing particles for each kind of virus. For example, Table 4 shows a case by way of example in which the disease information contains information with which a disease can be identified on the basis of the number of passing particles for each viral species or type especially when the virus is active.

For example, according to Table 4, if the number of passing particles of active herpes simplex virus 1 (HSV-1) is not less than a threshold value α (e.g., 30), the disease determining unit 14 determines HSV herpetic keratitis for which administration of an antiviral agent is effective. Since herpes simplex virus 1 may be counted (detected) even from a body fluid of a healthy subject depending on the stress state, if the number of passing particles is less than the threshold value α, there is no need to determine that the subject has a viral disease.

Furthermore, according to Table 4, if the number of passing particles of active varicella-zoster virus (VZV) is not less than a threshold value β (e.g., 1), the disease determining unit 14 determines VZV uveitis for which administration of an antiviral agent is effective. If the number of passing particles of active human cytomegalovirus (HCMV) is not less than a threshold value (e.g., 1), the disease determining unit 14 determines CMV corneal endotheliitis for which administration of an antiviral agent is effective. These viruses are never counted from a body fluid of a healthy subject, and therefore, if even a single virus particle is detected, the disease is identified.

TABLE 4

| Kind of virus | HSV-1 | VZV | ... | HCMV |
|---|---|---|---|---|
| Threshold value of number of passing particles | α | β | | ζ |
| Disease | HSV Herpetic keratitis | VZV Uveitis | | CMV Corneal endotheliitis |

In the present embodiment, the processing for determining the kind of a virus contained in a body fluid of a subject is implemented by causing the control unit 10 (CPU) to execute a virus determining program (hereinafter, also referred to simply as the "program") that implements this processing. This program causes the control unit 10 to obtain the waveform information from the measuring unit 7 (an example of receiving processing), causes the determining unit 11 of the control unit 10 to apply the obtained waveform information to the learned model (an example of virus determining processing), and furthermore, causes the control unit 10 to transmit the determination result to the output unit 92 or the like (an example of transmitting processing). This program can be stored in, for example, the storage unit 8. When the program is stored in the storage unit 8, it is preferable to store the storage unit 8 in a non-temporary storage medium (e.g., a magnetic storage medium, an optical disk, a flash memory, or the like).

(Flow of Virus Measurement and Disease Determination)

The flow of virus measurement will be described. In the following description, a case in which the storage unit 8 contains disease information such as that shown in Table 4 is taken as an example. A measurer or the like stores the specimen L1 in the specimen reservoir 2, and also stores the electrolytic solution L2 in the electrolytic solution reservoir 3. Then, the specimen L1 and the electrolytic solution L2 are brought into contact with each other via the through-hole 6 so that electricity can flow therebetween (contact step).

After putting the specimen L1 and the electrolytic solution L2 into a state in which electricity can flow therebetween, the measurer or the like inputs measurement conditions, such as the measurement time (a duration for which a voltage is applied and counting is continued) and a measurement start instruction to the control unit 10 via the input unit 91. Then, the control unit 10 instructs the power supply unit 71 to apply a voltage under conditions corresponding to the input measurement conditions. According to the instruction, the power supply unit 71 applies a voltage to the first electrode 72 under predetermined conditions.

In the present embodiment, the measurement time is preset to 5 minutes. As described above, when a learned model is used, the comparing unit 13 can determine the kind of virus with a sufficiently high probability by merely obtaining a single pulse. However, if the amount of virus (the number concentration of virus particles) in the specimen L1 is small, the application of the voltage and the like need to be continued until at least one virus particle is counted (detected). When the measurement time is set to be, for example, from 1 to 10 minutes, or preferably from 1 to 5 minutes, rapid and accurate virus determination can be achieved.

Normally, if no virus particle is counted even when the application of the voltage is continued for a predetermined period of time, the subject is healthy. For this reason, in the present embodiment, the measurement time is preset to 5 minutes, which is an estimate of the measurement time that is necessary and sufficient to determine whether or not the subject is healthy. In order to improve the accuracy of determination of whether or not the subject is healthy even more, the upper limit of the measurement time may be set to 10 minutes. Although the measurement time can be set to 10 minutes or longer, attention should be paid to the possibilities of the doctor's diagnosis being delayed or the patient waiting time being prolonged.

If the measurement time is set to be excessively short, a false determination that no virus is present (a false determination that the subject is healthy) may be made when the amount of virus contained is small. Therefore, it is preferable to secure a measurement time of at least 10 seconds.

Figure 16:
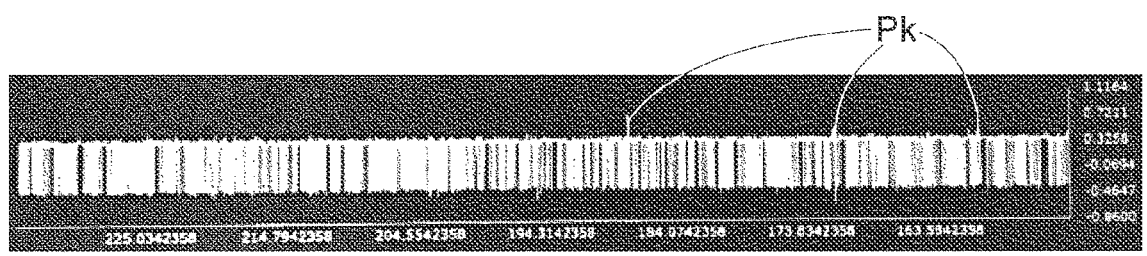
FIG. 16 shows an example of a waveform obtained from a specimen of a patient with HSV herpetic keratitis.
Figure 17:
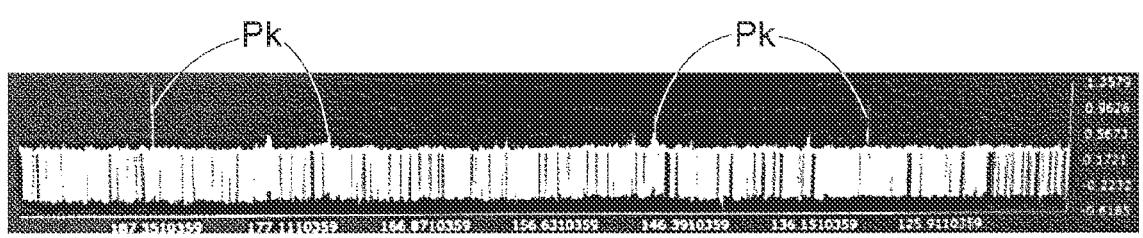
FIG. 17 shows an example of a waveform obtained from a specimen of a patient with CMV corneal endotheliitis.

When a predetermined voltage is applied to the first electrode 72, virus particles in the specimen L1 migrate toward the second electrode 73 due to electrophoresis. During this migration, when a virus particle passes through the through-hole 6, a peak Pk appears in the waveform of the ionic current (current measuring step, passing step). FIG. 16 shows an example of a waveform obtained from a specimen L1 of a patient with HSV herpetic keratitis. FIG. 17 shows an example of a waveform obtained from a specimen L1 of a patient with CMV corneal endotheliitis. In each of FIGS. 16 and 17, there are a plurality of peaks Pk.

The counting unit 12 identifies the occurrence of peaks Pk in the waveform, counts the number of identified peaks Pk as the number of passing particles, and sends the comparing unit 13 one trigger for each peak Pk.

Upon receiving a trigger, the comparing unit 13 applies the peak Pk corresponding to the trigger to the learned model read from the storage unit 8, thereby determining the kind of a virus that has caused the peak Pk (virus determining step). After determining the kinds of viruses, the comparing unit 13 sends information that contains the kinds of viruses to the counting unit 12. The counting unit 12 that has received the information containing the kinds of viruses counts the number of virus particles for each kind of virus.

The disease determining unit 14 identifies a disease on the basis of the kinds of viruses determined by the comparing unit 13, the number of virus particles counted by the counting unit 12 for each kind of virus, and the disease information that contains information such as that shown in Table 4. When the kinds of viruses have been determined, and the number of virus particles for each kind of virus has been counted, the disease determining unit 14 can identify a disease immediately (e.g., in real time).

For example, if the number of HSV herpetic keratitis particles is 19, the number of varicella-zoster virus (VZV) particles is 15, and the number of human cytomegalovirus (HCMV) particles is 0, VZV uveitis, for which administration of an antiviral agent is effective, is determined as the disease.

For example, if the number of HSV herpetic keratitis particles is 32, the number of varicella-zoster virus (VZV) particles is 0, and the number of human cytomegalovirus (HCMV) particles is 0, HSV herpetic keratitis and VZV uveitis, for which administration of an antiviral agent is effective, are determined as the diseases.

For example, if the number of HSV herpetic keratitis particles is 21, the number of varicella-zoster virus (VZV) particles is 0, and the number of human cytomegalovirus (HCMV) particles is 0, no disease is identified. In this case, instead of identifying a disease, it is also possible to identify that the subject is under high stress, as in the first embodiment.

Fourth Embodiment

Figure 18:
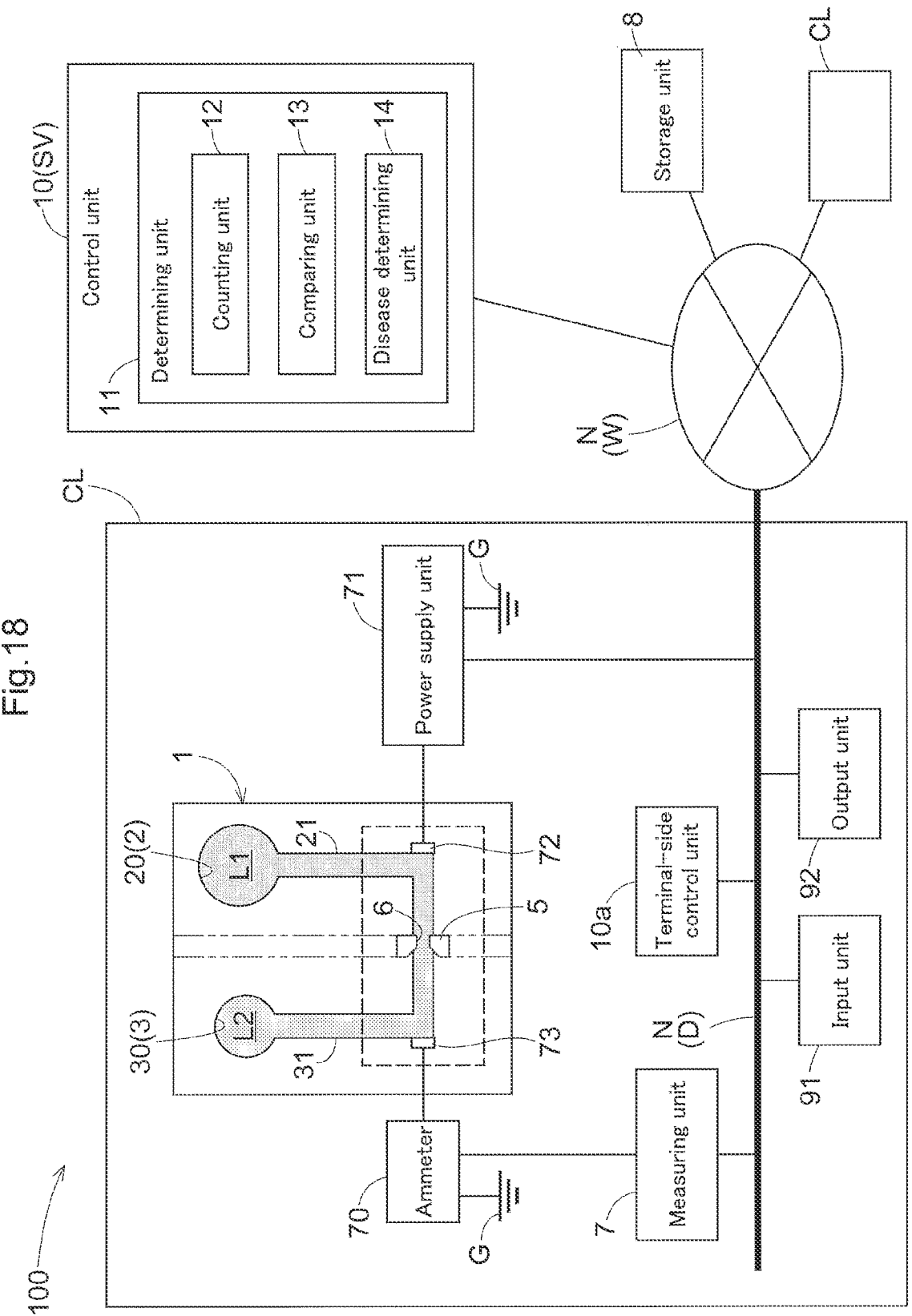
FIG. 18 is a schematic diagram showing the configuration of a measuring device of a fourth embodiment.

As a fourth embodiment, a case will be described in which, as shown in FIG. 18, a determining device 100 used as a virus measuring device is constituted by a terminal CL, a determining server SV, and a storage unit 8 that is a cloud server. The determining server SV and the terminal CL are connected to each other via the internet W (network N) such that two-way communication can be performed. FIG. 18 shows a case in which a plurality of (in FIG. 18, two) terminals CL are connected to the determining server SV such that two-way communication can be performed. In the following description, differences from the third embodiment will be described.

The determining server SV has a control unit 10. FIG. 18 shows, by way of example, a case in which the determining server SV is accessible to various kinds of information (including a learned model and a virus determining program) stored in the storage unit 8 via the network N, but the determining server SV may have the storage unit 8.

Each terminal CL has a test substrate 1, as well as a terminal-side control unit 10a, a measuring unit 7, a power supply unit 71, an input unit 91, and an output unit 92 that are connected via an internal bus D (network N) such that two-way communication can be performed.

The terminal-side control unit 10a communicates with the control unit 10 (determining server SV) via the internet W. The terminal-side control unit 10a controls operations of the test substrate 1, the measuring unit 7, the power supply unit 71, the input unit 91, and the output unit 92 on the basis of instructions from the control unit 10, as well as instructions and the like input from the input unit 91.

In the present embodiment, the processing for determining the kind of a virus contained in a body fluid of a subject is implemented by causing the determining server SV (control unit 10) to execute a virus determining program that implements this processing. This program causes the control unit 10 to obtain the waveform information from the terminal CL (an example of receiving processing), causes the determining unit 11 of the determining server SV to apply the obtained waveform information to the learned model (an example of virus determining processing), and further causes the determining server SV to transmit the determination result of the determining unit 11 to the terminal CL from which the waveform information has been obtained (an example of transmitting processing).

Note that, on the terminal CL, a terminal program is executed that causes the terminal CL to transmit the waveform information to the determining server SV (control unit 10), and receive the determination result from the determining server SV and output the received determination result from the output unit 92 or the like.

Figure 19:
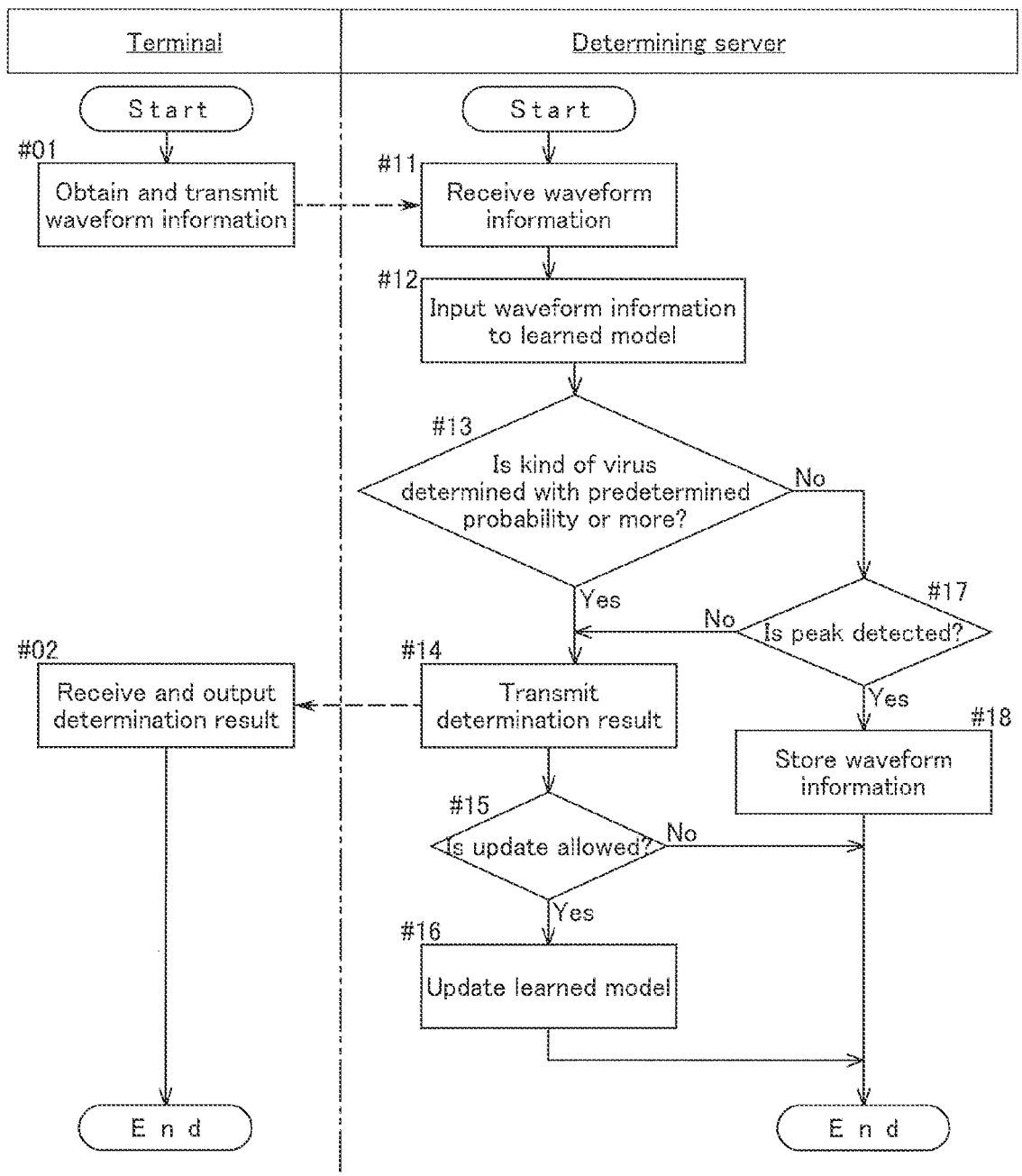
FIG. 19 shows the flow of operations executed by the determining device according to a virus determining program.

FIG. 19 shows an example of the flow of operations of this program. Hereinafter, the determining device 100 will be described with reference to FIG. 18, and the flow of operations of the determining device 100 will be described with reference to FIG. 19.

On the basis of, for example, a measurement start instruction that is input from the input unit 91, the terminal CL obtains the waveform information and transmits the waveform information to the determining server SV (#01). The determining server SV (control unit 10) receives the waveform information (#11).

The comparing unit 13 of the determining unit 11 inputs the received waveform information to the learned model (#12), and if the kind of virus is identified with a predetermined probability or more (e.g., 99% or more) (#13, Yes), the control unit 10 transmits the identified kind of virus to the terminal CL as the determination result (#14). In the terminal CL, the terminal-side control unit 10a receives the determination result transmitted from the determining server SV and outputs the determination result from the output unit 92 (#02), and then the processing is ended. The output determination result is consulted by the doctor and the like.

After the determination result is transmitted to the terminal CL (#14), if update of the learned model is allowed by default settings of the determining server SV (#15, Yes), the learned model is updated on the basis of the received waveform information (#16), and the processing is ended. If update of the learned model is not allowed by default settings of the determining server SV (#16, No), the processing is ended without updating the learned model. Note that the steps #15 and #16 may be skipped.

If the kind of virus is not determined with a predetermined probability or more (#13, No), and no peak Pk is detected (#17, No), the control unit 10 transmits a determination result to the effect that no virus is detected to the terminal CL (#14).

If the kind of virus is not determined with a predetermined probability or more (#13, No), but a peak Pk is detected (#17, Yes), the waveform information is stored (#18) for the purpose of compiling case records for the future reference, for example. Note that the step #18 may be skipped.

In this manner, the determining device 100 can also be implemented using network computing technologies, such as a client-server model or a cloud server model.

Variations of Embodiments (Variation 1)

In the foregoing embodiments, a case is described in which, when tear fluid of the subject is used as the body fluid, the conjunctival sac of the subject is flushed with phosphate-buffered saline (saline), and the flushing solution containing tear fluid is collected and used as the body fluid. In this case, the saline with which the conjunctival sac of the subject is flushed may contain an additive, in addition to salt (sodium chloride) and a buffer (pH regulator) such as sodium hydrogen phosphate.

Examples of the additive here include L-cysteine, homocysteine, glutathione, oxiglutathione, cysteine persulfide, glutathione persulfide, homocysteine persulfide, glucose, calcium chloride, magnesium chloride, and potassium chloride.

In the case where the saline contains oxiglutathione as an additive, the saline is preferably prepared such that the acidity or alkalinity (hydrogen ion exponent), that is, the pH thereof is about 7.1 to 8.1, and the osmotic pressure ratio thereof is about 1.0 to 1.1. For example, the acidity or alkalinity and the osmotic pressure ratio can be adjusted by adding sodium chloride, magnesium chloride, or potassium chloride, or sodium hydrogen phosphate, sodium hydrogen carbonate, sodium citrate, or sodium acetate, or the like.

In the case where the saline contains especially oxiglutathione as an additive, the accuracy of determination of the viral species of virus advantageously improves. The reason for this is that oxiglutathione contained in the saline increases the viral activity or prevents a decrease in the viral activity, thereby improving the storability of the specimen, and, thus, the shape of a peak Pk that depends on the viral species of virus can be detected even more clearly.

An example of the improvement of the accuracy of determination of the viral species of virus will be described below. First, the anterior chamber aqueous humor (an example of the aqueous humor) was collected, as the body fluid, from the eyeball of a patient with CMV iritis.

Next, a specimen (specimen A) was prepared by storing the collected anterior chamber aqueous humor as-is at 4° C. for 2 hours; a specimen (specimen B) was prepared by diluting the anterior chamber aqueous humor 2-fold with phosphate-buffered saline and then storing the diluted solution at 4° C. for 2 hours; and a specimen (specimen C) was prepared by diluting the anterior chamber aqueous humor 2-fold with a commercially available intraocular irrigating solution (product name: BSS PLUS 500 intraocular irrigating solution 0.0184%, manufacturing company: Alcon Japan Ltd.) containing oxiglutathione as an active ingredient, and then storing the diluted solution at 4° C. for 2 hours. The specimen C is equivalent to the specimen L1 of the present embodiment when containing oxiglutathione.

Furthermore, viruses in the specimens A, B, and C were measured using the determining device 100. The numbers of human cytomegalovirus particles detected (measurement time: 5 minutes) from the specimens A, B, and C, which contained the anterior chamber aqueous humor collected from the same patient, were 0, 7, and 12, respectively.

The detection results of human cytomegalovirus from the specimens A, B, and C show that, when a specimen L1 contains oxiglutathione, the virus detection accuracy improves, and the viral species determination accuracy improves accordingly.

(Variation 2)

In the foregoing embodiments, a case is described by way of example in which an electrolytic solution such as saline is used as the electrolytic solution L2. However, the electrolytic solution L2 may contain an additive, in addition to salt (sodium chloride).

Examples of the additive here include L-cysteine, homocysteine, glutathione, oxiglutathione, cysteine persulfide, glutathione persulfide, homocysteine persulfide, glucose, calcium chloride, magnesium chloride, potassium chloride, and other pH regulators. Examples of the pH regulators include sodium hydrogen phosphate, sodium hydrogen carbonate, sodium citrate, sodium acetate, and lactic acid.

In the case where the electrolytic solution L2 contains oxiglutathione as an additive, the electrolytic solution L2 is preferably prepared such that the acidity or alkalinity (hydrogen ion exponent), that is, the pH thereof is about 7.1 to 8.1, and the osmotic pressure ratio thereof is about 1.0 to 1.1. For example, the acidity or alkalinity and the osmotic pressure ratio can be adjusted by adding sodium chloride, magnesium chloride, or potassium chloride, or sodium hydrogen phosphate, sodium hydrogen carbonate, sodium citrate, or sodium acetate, or the like.

In the case where the electrolytic solution L2 contains especially oxiglutathione as an additive, the accuracy of determination of the viral species of virus advantageously improves. The reason for this is that oxiglutathione contained in the electrolytic solution L2 increases the viral activity or prevents a decrease in the viral activity, thereby improving the storability of the specimen, and, thus, the shape of a peak Pk that depends on the viral species of virus can be detected even more clearly.

EXAMPLES

Results of Clinical Diagnosis, Determination, or Detection for Each Case Hereinafter, the results of determination of the kind of virus using the determining device 100 shown in the third embodiment, the results of clinical diagnosis by a doctor, and the results of determination of the kind of virus by real-time PCR (hereinafter, referred to simply as "PCR") will be compared and described.

Table 4 shows the results of clinical diagnosis, the types of specimens, the results of determination using the determining device 100, and the results of detection by PCR, with respect to Cases 1 to 9. The specimens subjected to the determination using the determining device 100 were the same as those subjected to PCR. In clinical diagnosis of Cases 1 to 9, the doctor used neither the results of determination using the determining device 100 nor the results of detection by PCR.

The specimens subjected to the determination using the determining device 100 were collected from subjects and diluted 2-fold with a commercially available intraocular irrigating solution (product name: BSS PLUS 500 intraocular irrigating solution 0.0184%, manufacturing company: Alcon Japan Ltd.) containing oxiglutathione as an active ingredient. The measurement time of the determining device 100 was set to 5 minutes, and the viral species of active viruses were output (detected). The measurement time of PCR was set to about 3 hours, and the viral species were detected. Note that PCR is not capable of determining whether or not a virus is active.

TABLE 5

| Kind of virus | HSV-1 | VZV | ... | HCMV |
|---|---|---|---|---|
| Threshold value of number of passing particles | α | β | | ζ |
| Disease | HSV Herpetic keratitis | VZV Uveitis | | CMV Corneal endotheliitis |

With respect to Cases 1 and 3 to 6, the determining device 100 detected viruses corresponding to the results of clinical diagnosis; however, with PCR, viruses were not detected, and the specimens were determined as negative. With respect to Cases 2, 7, and 8, both the determining device 100 and PCR detected viruses corresponding to the clinical diagnoses. From these results, it is conceivable that the determining device 100 has high correlations with clinical diagnoses, and also has higher determination or detection sensitivity than PCR.

With respect to Case 9, in clinical diagnosis, CMV iritis, which is caused by infection with HCMV, was diagnosed, and PCR also detected HCMV. However, the determining device 100 did not detect an active virus. With respect to Case 9, the effect of an antiviral agent was not observed in the result of clinical diagnosis, and it is therefore conceivable that, at the time when the specimen of Case 9 was collected, no active virus was present in the specimen (in the body of the subject). Furthermore, it is conceivable that, in Case 9, an inactive virus leaked into the tear fluid and was detected by PCR.

As in Case 9, when a specific symptom or disease name (in Case 9, CMV iritis) can be clinically diagnosed, it is difficult for the doctor who is responsible for subjects health recovery to make a diagnosis to the effect that an active virus is not present in the body of the subject, or to decide to exclude a treatment (e.g., administration of an antiviral agent) that is effective if an active virus is present in the body of the subject from treatment options. However, with the determination result of the determining device 100, the doctor can obtain information to the effect the no active virus is present in the body of the subject, and can make a more appropriate diagnosis or select a more appropriate treatment strategy.

As described above, in view of Cases 1 to 9, it is conceivable that the doctor can make a more appropriate diagnosis on the basis of the result of detection of an active virus using the determining device 100.

In the above-described manner, a determining device can be provided with which a simple, rapid, and accurate virus measuring method, a virus measuring device that implements the virus measuring method, a virus determining program, a stress determining method, and a stress determining device that implements the stress determining method can be implemented.

OTHER EMBODIMENTS (1) In the description of the foregoing embodiments, herpes simplex virus 1 (HSV-1) is used as an example of the microparticles. However, the microparticles are not limited to herpes simplex virus 1 (HSV-1). Other species of herpesviruses, such as human cytomegalovirus (HCMV) and human herpesvirus 6 (HHV-6), may also be used as the microparticles, or viruses (viral species) other than herpesviruses, such as adenoviruses that do not have envelopes unlike herpesviruses, may be used as the microparticles.

Figure 11:
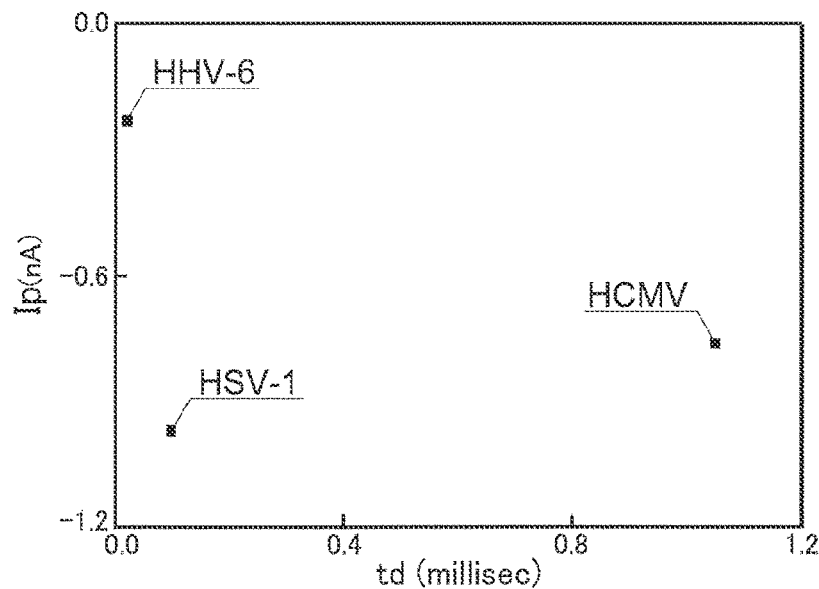
FIG. 11 is a graph showing an example of the peak shape for each viral species.

FIG. 11 shows the pulse height Ip and the pulse width td of the peaks Pk of three different viral species, HSV-1, HCMV, and HHV-6. As shown in FIG. 11, different viral species have different peak shapes, and it is possible to detect peaks Pk even when different viral species are present. Therefore, even when different viral species are present, the number of passing particles can be counted on the basis of the waveform.

(2) In the foregoing embodiments, a case is described in which the determining unit 11 has the counting unit 12 that counts the number of passing particles on the basis of the waveform and the comparing unit 13 that compares the number of passing particles with the stress state information, and the determining unit 11 determines the stress state of the subject on the basis of the number of passing particles and the stress state information. However, the present invention is not limited to this configuration.

For example, the determining unit 11 may further measure the shape of peaks Pk, such as the pulse height Ip and the pulse width td, using the counting unit 12 or the like and determine a viral species for each individual peak Pk. The determining unit 11 can also obtain the number of passing particles and the distribution of viral species in the obtained number of passing particles and determine the stress state of the subject by comparing the number of passing particles and the distribution with the stress state information. In addition, a configuration can also be adopted in which the determining unit 11 does not determine viral species, but obtains the number of passing particles and information regarding the distribution of the shapes of the peaks Pk, such as the pulse height Ip and the pulse width td, in the obtained number of passing particles and determines the stress state of the subject by comparing the number of passing particles and the distribution with the stress state information.

In the case where the stress state of the subject is determined by obtaining the distribution of viral species or obtaining the information regarding the distribution of the shapes of peaks Pk, the stress state information contains, as the stress state information, at least relation information on the relation between the number of virus particles for each viral species and the stress intensity, or relation information on the relation between the number of peaks Pk in the waveform, information regarding the distribution of the shapes of the peaks Pk, and the stress intensity, of specimens that have been collected beforehand under predetermined measurement conditions.

Now, level information on the stress intensity that can be contained in the relation information in the case where the stress state of the subject is determined by obtaining the distribution of viral species or obtaining the information regarding the distribution of the shapes of peaks Pk as described above will be described. For example, the relation information can contain level information on the stress intensity to the effect that the higher the amount of distribution of human herpesvirus 6 (HHV-6) is, the more strongly the subject feels long-term stress rather than short-term stress. On the basis of such relation information, in the case of a higher amount of distribution of HHV-6, the determining unit 11 can determine that the subject feels long-term stress more strongly, and in the case of a lower amount of distribution of HHV-6, the determining unit 11 can determine that the subject feels short-term stress more strongly.

(3) In the foregoing embodiments, a case is described in which the body fluid is tear fluid. However, the body fluid is not limited to tear fluid. For example, intraocular fluid such as, for example, eye's aqueous humor (also referred to simply as "aqueous humor") or vitreous humor, saliva, sweat, urine, or other body fluids may also be used.

(4) In the foregoing embodiments, a case is described by way of example in which the determination results are replaced with the terms that correspond to the stress intensity levels and by which the stress state can be intuitively understood, and such terms are indicated. However, the manner in which the determination results are indicated is not limited to this. For example, a configuration may also be adopted in which the determination results are replaced with jobs corresponding to the stress intensity levels, and such jobs are indicated. The indication can be performed in any form that enables a user who performs determination using the determining device 100, or a subject who is the target of determination using the determining device 100, to easily understand the type and the severity of external factors of stress, such as the duties and the working hours. In the present embodiment, for example, a case is conceivable in which the determination results are replaced with corresponding hospital jobs, such as nurse.

(5) In the foregoing embodiments, jobs in hospitals and the like, such as nurse, are provided as examples of the external factors of stress according to which the stress input levels are categorized. However, the external factors of stress are not limited to this. For example, the commuting time, the working hours, the time of day worked, or the like may be adopted, or these factors may be added and used.

(6) In the foregoing embodiments, a case is described by way of example in which the inner surface 6a of the through-hole 6 is surface-treated so as to have a surface charge of the same polarity as virus, that is, a negative surface charge. However, surface modification is not necessarily needed, and a case is also conceivable in which surface modification is not performed.

(7) In the foregoing embodiments, a case is described in which the disease information contains the information with which the disease determining unit 14 can identify a disease on the basis of the kinds of viruses and the number of passing particles for each kind of virus. However, the disease information is not limited to this information, and can also contain other pieces of information. For example, the disease information may contain information with which the disease determining unit 14 can determine one disease, or a plurality of likely diseases, corresponding to a combination of the kinds of viruses and the amount (number) of virus particles for each kind of virus. Furthermore, in the case where a plurality of diseases are identified corresponding to a combination of the kinds of viruses and the amount (number) of virus particles for each kind of virus, the disease information may contain information with which the disease determining unit 14 can identify diseases in order of likelihood of validity (e.g., probability).

(8) In the first to third embodiments above, a case is described in which the determining device 100 includes the test substrate 1 serving as a test chip, the measuring unit 7 that obtains the waveform from the test substrate 1, the control unit 10, such as the CPU, that determines the stress state of the subject on the basis of information obtained from the test substrate 1, and the power supply unit 71, and the measuring unit 7 and other units are connected to the control unit 10 via the network N. However, the configuration of the determining device 100 is not limited to this case.

For example, the determining device 100 can be made easily portable by forming, as a determining device main body (not shown), the control unit 10, the measuring unit 7, and the network N as a single unit. In addition, the test substrate 1 can be made easily portable by forming it as a test chip that can be connected to, or installed in, and disconnected from, or removed from, the determining device main body as desired.

Furthermore, in this case, as a result of the test substrate 1 being able to be freely attached to and detached from the determining device main body, it is possible to collect and store the body fluid into the test substrate 1 near the patient and then easily move (transport) only the test substrate 1 in which the body fluid is stored, and the convenience can thus be improved. Moreover, cross-contamination can be prevented by preparing a plurality of test substrates 1 for a determining device 100 and using each of the test substrates 1 exclusively for a single patient, or using the test substrates 1 in a disposable manner.

(9) In the fourth embodiment above, a case is described in which the terminal CL has the test substrate 1 as well as the terminal-side control unit 10a, the measuring unit 7, the power supply unit 71, the input unit 91, and the output unit 92 that are connected via the internal bus D (network N) such that two-way communication can be performed. However, the configuration of the terminal CL is not limited to this case.

For example, the terminal CL can be made easily portable by forming, as a determining device main body (not shown), the terminal-side control unit 10a, the measuring unit 7, the power supply unit 71, and the internal bus D as a single unit. In addition, the test substrate 1 can be made easily portable by forming it as a test chip that can be connected to, or installed in, and disconnected from, or removed from, the determining device main body as desired.

Furthermore, in this case, as a result of the test substrate 1 being able to be freely attached to and detached from the determining device main body, it is possible to collect and store the body fluid into the test substrate 1 near the patient and then easily move (transport) only the test substrate 1 in which the body fluid is stored, and the convenience can thus be improved. Moreover, cross-contamination can be prevented by preparing a plurality of test substrates 1 for a determining device 100 and using each of the test substrates 1 exclusively for a single patient, or using the test substrates 1 in a disposable manner, and the determination accuracy can thus be improved.

(10) In the foregoing embodiments, herpes simplex virus 1 (HSV-1 (HHV1)), varicella-zoster virus (VZV (HHV3)), human cytomegalovirus (HCMV (HHV5)), and human herpesvirus 6 (HHV-6) are used as examples of the virus (especially, herpesvirus). However, the virus that can be determined by the determining device 100 is not limited to these viruses. The determining device 100 is capable of determining various kinds of herpesviruses including at least human herpesviruses HHV1 to 8. Also, the determining device 100 is capable of determining the kinds of viruses other than herpesviruses, such as adenoviruses, enteroviruses, coxsackieviruses, human papillomaviruses, rubella viruses, and other viruses of clinical importance.

(11) In the third embodiment above, a learned model with which, when a peak Pk caused by a certain kind of virus (e.g., active herpes simplex virus 1) is input, the kind of virus can be determined is described as an example of the learned model (waveform information). However, the kinds of viruses that can be learned by the learned model are not limited to active viruses but also include inactive viruses. As a result of making the learned model learn both the peaks Pk of active viruses and the peaks Pk of inactive viruses, the comparing unit 13 can easily determine the activity or inactivity as the kind of virus. Thus, the disease determining unit 14 can determine a disease taking whether the virus is active or inactive into account.

(12) In the description of the flow of virus measurement of the third embodiment above, a case is described by way of example in which the disease information stored in the storage unit 8 contains information, such as that shown in Table 4, with which a disease can be identified on the basis of the number of passing particles for each viral species or type especially when the virus is active, and the disease determining unit 14 determines that the identified disease is a disease for which administration of an antiviral agent is effective. However, the disease information stored in the storage unit 8 may contain information with which a disease can be identified taking the differences in viral species and type as well as whether the virus is active or inactive into account. In this case, the disease determining unit 14 can perform determination by distinguishing between a disease for which administration of an antiviral agent is effective and a disease for which administration of an antiviral agent is not effective, even when the diseases are the same disease (e.g., VZV uveitis).

For example, if active virus particles and inactive virus particles are counted, especially if the number of active virus particles counted is greater than that of inactive virus particles, the disease determining unit 14 determines a disease for which administration of an antiviral agent is effective.

For example, if only inactive virus particles are counted, or if active virus particles and inactive virus particles are counted, but the majority (e.g., 80%) of the total number of passing virus particles that are counted are inactive virus particles, the disease determining unit 14 determines a disease for which administration of an antiviral agent is not effective. As used herein, the "disease for which administration of an antiviral agent is not effective" means, for example, a disease that is clinically diagnosed as a disease caused by a virus but the patient is already in a state of recovery due to the immune functions in the patient's body (elimination of the virus is nearing completion) and hence a state in which administration of an antiviral agent does no longer contribute to the treatment or the improvement in quality of life (QOL) of the patient.

Note that a configuration disclosed in one of the foregoing embodiments (including the other embodiments, the same shall apply hereinafter) can be used in combination with a configuration of any other embodiments as long as there is no contradiction. Moreover, the embodiments disclosed herein should be considered as illustrative and not limiting embodiments of the present invention, and appropriate modifications can be made thereto without departing from the object of the present invention.

INDUSTRIAL APPLICABILITY

The present invention is applicable to a simple, rapid, and accurate virus measuring method, a virus measuring device, a virus determining program, a stress determining method, and a stress determining device.

REFERENCE SIGNS LIST

2: specimen reservoir
3: electrolytic solution reservoir
5: separating wall
6: through-hole (through-hole portion)
7: measuring unit
8: storage unit
10: control unit
10*a*: terminal-side control unit
11: determining unit (stress determining unit)
12: counting unit
13: comparing unit (virus determining unit)
14: disease determining unit
15: life information determining unit
16: learning unit
17: matching degree determining unit
18: updating unit
70: ammeter
91: input unit
100: determining device (stress determining device, virus measuring device)
L1: specimen
L2: electrolytic solution
V: virus

The invention claimed is:
1. A virus measuring method comprising:
a contact step of bringing a liquid specimen containing a body fluid of a subject, the body fluid being selected from tear fluid and intraocular fluid, and an electrolytic solution into contact with each other via a through-hole portion formed in a separating wall, the through-hole portion including an inner surface having hydrophilicity and a surface charge of the same polarity as a polarity of a herpes virus contained in the body fluid;
a current measuring step of applying a voltage to the liquid specimen and the electrolytic solution with respect to the through-hole portion and obtaining a waveform of an ionic current flowing through the through-hole portion; and
a virus determining step of determining the kind of the herpes virus contained in the body fluid on the basis of the waveform,
wherein, in the virus determining step, the waveform is compared with waveform information that corresponds to a known herpes virus and is obtained beforehand, and the kind of the herpes virus is determined.

2. The virus measuring method according to claim 1, wherein the current measuring step includes a passing step of causing a microparticle contained in the body fluid to electrophoretically migrate and pass through the through-hole portion.

3. The virus measuring method according to claim 1, wherein the current measuring step includes a separation step of separating a herpes virus contained in the body fluid and impurities other than the herpes virus contained in the body fluid using an electroosmotic flow.

4. The virus measuring method according to claim 1, wherein a disease is identified on the basis of the kind of the herpes virus that has been determined in the virus determining step.

5. The virus measuring method according to claim 1, wherein the liquid specimen contains oxiglutathione.

6. A virus measuring device comprising:
a specimen reservoir configured to store a liquid specimen containing a body fluid of a subject, the body fluid being selected from tear fluid and intraocular fluid;
an electrolytic solution reservoir configured to store an electrolytic solution;
a separating wall portion that separates the specimen reservoir and the electrolytic solution reservoir;
a through-hole portion that is formed in the separating wall portion and through which the specimen reservoir and the electrolytic solution reservoir are in communication with each other, the through-hole portion including an inner surface having hydrophilicity and a surface charge of the same polarity as a polarity of a herpes virus contained in the body fluid;
a measuring unit configured to apply a voltage to the liquid specimen and the electrolytic solution and obtain a waveform of an ionic current flowing through the through-hole portion;
a storage unit in which a learned model is stored, the learned model being created by performing machine learning so that, when the waveform is input to the learned model, the learned model outputs a herpes viral species corresponding to waveform information on a known herpes viral species; and
a virus determining unit configured to apply the waveform obtained from the measuring unit to the learned model read from the storage unit and thereby determine the kind of the herpes virus contained in the body fluid.

7. The virus measuring device according to claim 6, wherein the liquid specimen contains oxiglutathione.

8. The virus measuring device according to claim 6, wherein the virus measuring device is portable.

9. A virus measuring device comprising:
a specimen reservoir configured to store a liquid specimen containing a body fluid of a subject, the body fluid being selected from tear fluid and intraocular fluid;
an electrolytic solution reservoir configured to store an electrolytic solution;
a separating wall portion that separates the specimen reservoir and the electrolytic solution reservoir;
a through-hole portion that is formed in the separating wall portion and through which the specimen reservoir and the electrolytic solution reservoir are in communication with each other, the through-hole portion including an inner surface having hydrophilicity and a surface charge of the same polarity as a polarity of a herpes virus contained in the body fluid;
a measuring unit configured to apply a voltage to the liquid specimen and the electrolytic solution and obtain a waveform of an ionic current flowing through the through-hole portion;
a storage unit in which waveform information on a known herpes viral species is stored; and
a virus determining unit configured to determine the kind of the herpes virus contained in the body fluid on the basis of the waveform,
wherein the virus determining unit is configured to determine the kind of the herpes virus contained in the body fluid by comparing the waveform obtained from the measuring unit with the waveform information on the known herpes viral species read from the storage unit.

10. The virus measuring device according to claim 9, wherein the liquid specimen contains oxiglutathione.

* * * * *